US009082182B2

(12) United States Patent
Sebok

(10) Patent No.: US 9,082,182 B2
(45) Date of Patent: Jul. 14, 2015

(54) EXTRACTING PATIENT MOTION VECTORS FROM MARKER POSITIONS IN X-RAY IMAGES

(75) Inventor: David Sebok, Eagleville, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 877 days.

(21) Appl. No.: 12/700,028

(22) Filed: Feb. 4, 2010

(65) Prior Publication Data

US 2011/0123088 A1 May 26, 2011

Related U.S. Application Data

(63) Continuation-in-part of application No. 12/626,197, filed on Nov. 25, 2009, now Pat. No. 8,363,919.

(51) Int. Cl.
*G06K 9/00* (2006.01)
*G06T 7/00* (2006.01)
(Continued)

(52) U.S. Cl.
CPC ............. *G06T 7/0042* (2013.01); *G06T 11/005* (2013.01); *A61B 6/583* (2013.01); *G06T 2207/10116* (2013.01); *G06T 2207/30204* (2013.01); *G06T 2211/412* (2013.01)

(58) Field of Classification Search
CPC ..................................................... G06T 7/0042
USPC .................................................. 382/128-133
See application file for complete search history.

(56) References Cited

U.S. PATENT DOCUMENTS 3,109,588 A 11/1963 Polhemus et al.
4,709,333 A 11/1987 Crawford (Continued)

FOREIGN PATENT DOCUMENTS

CN 1475971 2/2004
CN 101489033 7/2009

(Continued)

OTHER PUBLICATIONS

Lee, K.J., Kwon, D., Yun, I.D., Lee, S.U.: "Deformable 3d volume registration using efficient MRFS model with decomposed nodes", British Machine Vision Conference (2008).*

(Continued)

*Primary Examiner* — Robert Sorey
(74) *Attorney, Agent, or Firm* — Michael Best & Friedrich LLP

(57) ABSTRACT

A method and a system for determining patient motion in an image. The method includes obtaining an image based on image data generated by a scanner during a scan. The image includes at least three markers assumed to be in a rigid or semi-rigid configuration. Each of the at least three markers has actual measured positions on a detector panel of the scanner in a first dimension and a second dimension. The method further includes determining a reference three-dimensional position for each of the at least three markers and defining equations describing the relationship between the reference three-dimensional position and the actual measured positions of each of the at least three markers, geometric parameters of the scanner, and patient motion. The method finally includes solving numerically the equations to derive a six-component motion vector describing patient motion for the image that accounts for differences between the reference three-dimensional position of each of the at least three markers and the actual measured positions for each of the at least three markers.

21 Claims, 9 Drawing Sheets

(51) Int. Cl.
*G06T 11/00* (2006.01)
*A61B 6/00* (2006.01)

(56) References Cited

U.S. PATENT DOCUMENTS 5,023,894 A 6/1991 Yamashita et al.
5,109,397 A 4/1992 Gordon et al.
5,339,367 A 8/1994 Roth
5,359,637 A 10/1994 Webber
5,442,674 A 8/1995 Picard et al.
5,668,844 A 9/1997 Webber
5,676,673 A 10/1997 Ferre et al.
5,769,789 A 6/1998 Wang et al.
5,771,306 A 6/1998 Stork et al.
5,871,445 A 2/1999 Bucholz
6,006,126 A 12/1999 Cosman
6,021,222 A 2/2000 Yamagata
6,081,577 A 6/2000 Webber
6,148,058 A 11/2000 Dobbs
6,243,439 B1 6/2001 Arai et al.
6,246,900 B1 6/2001 Cosman et al.
6,314,310 B1 11/2001 Ben-Haim et al.
6,330,356 B1 * 12/2001 Sundareswaran et al. .... 382/154
6,359,960 B1 3/2002 Wahl et al.
6,370,271 B2 4/2002 Fu et al.
6,385,632 B1 5/2002 Choe et al.
6,405,072 B1 6/2002 Cosman
6,484,048 B1 11/2002 Hoshino et al.
6,549,607 B1 4/2003 Webber
6,738,656 B1 5/2004 Ferre et al.
6,766,056 B1 7/2004 Huang et al.
6,856,827 B2 2/2005 Seeley et al.
6,859,555 B1 2/2005 Fang et al.
6,888,924 B2 5/2005 Claus et al.
6,973,202 B2 12/2005 Mostafavi
7,002,342 B2 2/2006 Duerk et al.
7,027,618 B2 4/2006 Trajkovic et al.
7,084,868 B2 8/2006 Farag et al.
7,110,614 B2 9/2006 Launay et al.
7,133,042 B2 11/2006 Anh et al.
7,207,715 B2 4/2007 Yue
7,221,728 B2 5/2007 Edic et al.
7,239,908 B1 * 7/2007 Alexander et al. ............ 600/427
7,258,674 B2 8/2007 Cribbs et al.
7,312,795 B2 12/2007 Aso et al.
7,336,765 B1 2/2008 Amiton et al.
7,340,108 B2 3/2008 Florent et al.
7,426,256 B2 9/2008 Rasche et al.
7,494,277 B2 2/2009 Setala
7,499,576 B2 3/2009 Setala
7,519,412 B2 4/2009 Mistretta
7,532,705 B2 5/2009 Yin et al.
7,545,909 B2 6/2009 Singh et al.
7,591,793 B2 9/2009 Orito et al.
7,646,899 B2 1/2010 Fitzpatrick
7,796,787 B2 * 9/2010 Wang et al. .................. 382/118
7,991,107 B2 8/2011 Sadakane et al.
8,116,544 B2 2/2012 Masumoto
8,180,130 B2 5/2012 Sebok
8,364,245 B2 1/2013 Kruecker
8,559,691 B2 10/2013 Borghese et al.
2002/0065461 A1 5/2002 Cosman
2002/0085668 A1 7/2002 Blumhofer et al.
2002/0109795 A1 8/2002 Bruzzone et al.
2002/0122536 A1 9/2002 Kerrien et al.
2003/0130576 A1 7/2003 Seeley et al.
2003/0228044 A1 12/2003 Gopalasamy et al.
2004/0114033 A1 6/2004 Eian et al.
2004/0136590 A1 7/2004 Brouwer
2005/0030076 A1 * 2/2005 Mohanavelu et al. ........ 327/165
2005/0059879 A1 3/2005 Sutherland et al.
2005/0059887 A1 3/2005 Mostafavi et al.
2005/0078861 A1 * 4/2005 Usikov .......................... 382/131
2005/0165292 A1 7/2005 Simon et al.
2006/0133564 A1 6/2006 Langan et al.
2006/0147100 A1 * 7/2006 Fitzpatrick .................... 382/131
2006/0245628 A1 11/2006 Jeung et al.
2007/0047794 A1 3/2007 Lang et al.
2007/0076938 A1 4/2007 Hartman et al.
2007/0106152 A1 * 5/2007 Kantrowitz et al. .......... 600/424
2007/0160270 A1 7/2007 Arini et al.
2007/0221850 A1 9/2007 Panin et al.
2007/0238947 A1 10/2007 Pescatore et al.
2007/0253599 A1 11/2007 White et al.
2007/0286470 A1 12/2007 Bernard et al.
2007/0291895 A1 12/2007 Yin et al.
2008/0021297 A1 1/2008 Boosten
2008/0037853 A1 2/2008 Bernard et al.
2008/0069418 A1 * 3/2008 Bystrov et al. ................ 382/131
2008/0075348 A1 3/2008 Rappaport et al.
2008/0101673 A1 * 5/2008 Fu et al. ........................ 382/128
2008/0159612 A1 7/2008 Fu et al.
2008/0221431 A1 9/2008 Steinmeyer et al.
2008/0267455 A1 10/2008 Grass et al.
2008/0267482 A1 * 10/2008 Abe et al. ...................... 382/131
2009/0022266 A1 1/2009 Stayman et al.
2009/0076369 A1 3/2009 Mistretta
2009/0122866 A1 5/2009 Crawford et al.
2009/0129634 A1 5/2009 De Waele
2009/0169080 A1 7/2009 Noordhoek
2009/0187096 A1 7/2009 Tiernan et al.
2009/0268865 A1 10/2009 Ren et al.
2010/0040274 A1 2/2010 Zhang et al.
2010/0099979 A1 * 4/2010 Schoonenberg et al. ..... 600/424
2010/0254583 A1 10/2010 Chan et al.
2010/0280375 A1 11/2010 Zhang et al.
2011/0123080 A1 5/2011 Sebok
2011/0123081 A1 5/2011 Sebok et al.
2011/0123085 A1 5/2011 Sebok
2011/0123088 A1 5/2011 Sebok
2011/0176723 A1 * 7/2011 Ali et al. ....................... 382/154
2013/0338492 A1 12/2013 Munro et al.
2014/0253113 A1 9/2014 Suzuki

FOREIGN PATENT DOCUMENTS

JP 01212570 8/1989
JP 06142093 5/1994
JP 0759763 3/1995
JP 0810265 1/1996
JP 10145335 5/1998
JP 2000316837 11/2000
JP 2001017422 1/2001
JP 0187283 4/2001
JP 03132356 5/2003
JP 2003305032 10/2003
JP 2004363850 12/2004
JP 2005021345 1/2005
JP 2005021675 1/2005
JP 2005296340 10/2005
JP 2005319207 11/2005
JP 2005324015 11/2005
JP 2006231051 9/2006
JP 2007016220 1/2007
JP 2007316809 6/2007
JP 2007244737 9/2007
JP 2008142543 6/2008
JP 2010535051 11/2010
JP 2011253433 12/2011
WO 01/01859 1/2001
WO 01/52190 7/2001
WO 2007/102509 9/2007

OTHER PUBLICATIONS

Debrunner, Christian, et al., "Tomographic Reconstruction from an Uncontrolled Sensor Trajectory", IEEE, 0-7803-8388-5/04, pp. 1416-1419, 2004.
Marchant, T.E., et al., "Measurement of Inter and Intra Fraction Organ Motion in Radiotherapy Using Cone Beam CT Projection Images", Physics in Medicine and Biology, vol. 53, No. 4, pp. 1087-1098, Feb. 21, 2008.
Seslija, Petar, et al., "Feasibility of 3D Tracking of Surgical Tools Using 2D Single Plane X-Ray Projections", Progress in Biomedical

(56) References Cited

OTHER PUBLICATIONS

Optics and Imaging—Proceedings of SPIE, vol. 6918, Medical Imaging 2008: Visualization, Image-Guided Procedures, and Modeling, San Diego, CA, Feb. 17-19, 2008.

Hannaford, Blake, et al., "Adaptive Linear Predictor Tracks Implanted Radiopaque Markers", IEEE Transactions on Biomedical Engineering, vol. BME-32, No. 2, pp. 117-125, Feb. 1985.

Owen, Rebecca, et al., "The Detectability and Localization Accuracy of Implanted Fiducial Markers Determined on In-Room Computerized Tomography (CT) and Electronic Portal Images (EPI)", Medical Dosimetry, vol. 33, No. 3, pp. 226-233, Elsevier, 2008.

Cucchiara, Rita, et al., "An Image Analysis Approach for Automatically Re-Orienteering CT Images for Dental Implants", Computerized Medical Imaging and Graphics, vol. 28, pp. 185-201, Elsevier, 2004.

Perrenot, Beatrice, et al., "Motion Compensation for 3D Tomographic Reconstruction of Stent in X-Ray Cardiac Rotational Angiography", IEEE, 0-7803-9577-8/06, pp. 1224-1227, ISBI 2006.

Mao, W., et al., "Fast Internal Marker Tracking Algorithm for Onboard MV and kV Imaging Systems", Medical Physics, vol. 35, No. 5, pp. 1942-1949, May 2008.

Pouliot, Sebastien, et al., "Automatic Detection of Three Radio-Opaque Markers for Prostate Targeting Using EPID During External Radiation Therapy", IEEE, 0-7803-6725-1/01, vol. 2, pp. 857-860, 2001.

Perrenot, Beatrice, et al., "Motion Correction for Coronary Stent Reconstruction from Rotational X-Ray Projection Sequences", IEEE Transactions on Medical Imaging, vol. 26, issue 10, pp. 1412-1423, Oct. 2007.

Aubry, Jean-Francois, et al., "Measurements of Intrafraction Motion and Interfraction Rotation of Prostate by Three-Dimensional Analysis of Daily Portal Imaging with Radiopaque Markers", International Journal of Radiation Oncology Biology Physics, vol. 60, No. 1, pp. 30-39, 2004.

Civco Medical Solutions, ISOLOC Software, available online at: <http://www.civco.com/oncology/localization/isoloc-software/>, available at least as early as Feb. 18, 2009.

Yue, Ning, et al., "A Method to Implement Full Six-Degree Target Shift Corrections for Rigid Body in Image-Guided Radiotherapy", Med. Phys., vol. 33, issue 1, pp. 21-31, Jan. 2006.

Canon, R.M., et al., "Analysis of Fiducial Markers Used for On-Line Verification in the External-Beam Radiotherapy of Patients with Cranial Tumours", Clinical and Translational Oncology, pp. 531-536, 2007.

Non-Final Office Action from the United States Patent and Trademark Office for U.S. Appl. No. 12/626,268 dated Apr. 15, 2011 (16 pages).

International Search Report and Written Opinion in International Application No. PCT/US2010/046828 dated Oct. 20, 2010, 14 pages.

International Search Report and Written Opinion in International Application No. PCT/US2010/46830 dated Oct. 22, 2010, 12 pages.

International Search Report and Written Opinion in International Application No. PCT/US2010/046834 dated Oct. 25, 2010, 11 pages.

International Search Report and Written Opinion in International Application No. PCT/US2010/46836 dated Oct. 13, 2010, 15 pages.

International Search Report and Written Opinion in International Application No. PCT/US2010/046845 dated Oct. 18, 2010, 11 pages.

International Search Report and Written Opinion in International Application No. PCT/US2010/046847 dated Oct. 25, 2010, 14 pages.

Office Action from the United States Patent and Trademark Office for U.S. Appl. No. 12/626,310 dated Oct. 30, 2012 (26 pages).

Office Action from the United States Patent and Trademark Office for U.S. Appl. No. 12/700,032 dated Sep. 11, 2012 (20 pages).

Notice of Allowance from the United States Patent and Trademark Office for U.S. Appl. No. 12/626,197 dated Oct. 2, 2012 (10 pages).

Hayashi, "Three Dimensional Analysis of Orthodontic Tooth Movement Based on XYZ and Finite Helical Axis System," Oct. 18, 2007, The European Journal of Orthodontic Advance Access, pp. 1-4.

Japanese Office Action for Japanese Patent Application No. 2012-541074 dated Apr. 11, 2014 (3 pages).

Korean Office Action for Korean Patent Application No. 10-2012-7016387 dated Apr. 15, 2014 (7 pages).

Japanese Office Action for Japanese Patent Application No. 2012-541075 dated May 2, 2014 (1 page).

Japanese Notice of Allowance for Japanese Patent Application No. 2012-541076 dated May 29, 2014 (3 pages).

First Office Action for Chinese Patent Application No. 201080062135.0 dated Apr. 3, 2014 (11 pages).

Japanese Office Action for Japanese Patent Application No. 2012-541073 dated Apr. 11, 2014 (6 pages).

Office Action from the Japanese Patent Office for Application No. 2012-541073 dated Aug. 30, 2013 (English Translation, 4 pages).

Office Action from the Korean Patent Office for Application No. 10-2012-7016387 dated Aug. 30, 2013 (English Translation and Original, 5 pages).

Office Action from the Japanese Patent Office for Application No. 2012-541074 dated Aug. 30, 2013 (English Translation, 3 pages).

Office Action from the Korean Patent Office for Application No. 10-2012-7016386 dated Aug. 23, 2013 (English Translation and Original, 5 pages).

Office Action from the Japanese Patent Office for Application No. 2012-541075 dated Aug. 20, 2013 (English Translation, 2 pages).

Office Action from the Korean Patent Office for Application No. 10-2012-7016513 dated Sep. 17, 2013 (English Translation and Original, 5 pages).

Office Action from the Japanese Patent Office for Application No. 2012-541076 dated Aug. 19, 2013 (English Translation, 2 pages).

Notice of Allowance from the United States Patent and Trademark Office for U.S. Appl. No. 13/716,860 dated Mar. 5, 2013 (20 pages).

Office Action from the United States Patent and Trademark Office for U.S. Appl. No. 12/700,032 dated Feb. 14, 2013 (24 pages).

Office Action from the United States Patent and Trademark Office for U.S. Appl. No. 12/626,310 dated Apr. 3, 2013 (30 pages).

Office Action from the United States Patent and Trademark Office for U.S. Appl. No. 12/626,218 dated Jun. 7, 2013 (14 pages).

Korean Patent Office Action for Application No. 10-2012-7016328 dated Oct. 31, 2013 (7 pages, English translation included).

Manoharan, "Validation of PET/CT Dataset for radiation treatment planning", Master's Thesis, Louisiana State University and Agricultural and Mechanical College, 133 pages, 2004.

Sun et al., "Automatic Segmentation of Fiducial Marks Using Attribute-based Mathematical Morphology" Journal of Electronic Imaging, vol. 10, No. 2, pp. 560-566, 2001.

Wiersma et al., Combining kV and MV imaging for real-time tracking of implanted fiducial markers:, Medical Physics, vol. 35, No. 4, pp. 1191-1198, 2008.

Navab et al., Dynamic Geometrical Calibration for 3-D Cerebral Angiography, SPIE, vol. 2708, pp. 361-370, 1996.

Chinese Patent Office Action for Application No. 201080062365.7 dated Jan. 8, 2014 (14 pages).

United States Patent Office Notice of Allowance for U.S. Appl. No. 12/626,218 dated Feb. 21, 2014 (11 pages).

United States Patent Office Action for U.S. Appl. No. 12/626,310 dated Feb. 12, 2014 (14 pages).

Flask, C. et al., "A method for fast 3D tracking using tuned fiducial markers and a limited projection reconstruction FISP (LPR-FISP) sequence", Journal of Magnetic Resonance Imaging, vol. 14, Issue 5, pp. 617-627, 2001.

First Office Action from the State Intellectual Property Office of the People's Republic of China for Application No. 201080062385.4 dated Apr. 30, 2014 (15 pages).

Chinese Patent Office Action for Application No. 201080062012.7 dated Jun. 18, 2014 (27 pages—with translation).

Final Office Action from the United States Patent and Trademark Office for U.S. Appl. No. 12/626,310 dated Sep. 10, 2014 (18 pages).

Office Action from the Korean Patent Office for Application No. 10-2012-7016387 dated Nov. 19, 2014 (5 pages).

(56) References Cited

OTHER PUBLICATIONS

Notice of Allowance from the Japanese Patent Office for Application No. 2012-541073 dated Dec. 3, 2014 (4 pages).
Notice of Allowance from the United States Patent and Trademark Office for U.S. Appl. No. 12/626,310 dated Jan. 7, 2015 (10 pages).
Office Action for Japanese Patent Application No. 2013-262534 dated Dec. 2, 2014 (2 pages).
Notice of Preliminary Rejection from the Korean Intellectual Property Office for Application No. 10-2015-7002525 dated Feb. 16, 2015 (6 pages).
2nd Office Action from The State Intellectual Property Office of the People's Republic of China for Application No. 201080062385.4 dated Mar. 9, 2015 (15 pages).

* cited by examiner

EXTRACTING PATIENT MOTION VECTORS FROM MARKER POSITIONS IN X-RAY IMAGES

RELATED APPLICATIONS

The present patent application is a continuation-in-part of co-pending U.S. patent application Ser. No. 12/626,197, filed on Nov. 25, 2009, entitled "MARKER IDENTIFICATION AND PROCESSING IN X-RAY IMAGES," the entire contents of which are all hereby incorporated by reference. The present application is also related to application Ser. No. 12/700,032, entitled "CORRECTING AND RECONSTRUCTING X-RAY IMAGES USING PATIENT MOTION VECTORS EXTRACTED FROM MARKER POSITIONS IN X-RAY IMAGES," and application Ser. No. 12/626,218, entitled "METHOD FOR ACCURATE SUB-PIXEL LOCALIZATION OF MARKERS ON X-RAY IMAGES," and application Ser. No.12/626,268, entitled "METHOD FOR X-RAY MARKER LOCALIZATION IN 3D SPACE IN THE PRESENCE OF MOTION," and application Ser. No. 12/626,310, entitled "METHOD FOR TRACKING X-RAY MARKERS IN SERIAL CT PROJECTION IMAGES."

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Embodiments of the invention relate to image processing. In particular, embodiments of the invention provide methods and systems for extracting patient motion vectors from marker positions in x-ray images and using the vectors to correct reconstructed images for patient and other unplanned motion.

SUMMARY

Modern imaging systems acquire many images during a single procedure or scan. The images are combined using a process known as reconstruction to produce one or more images representing finite-width "slices" through a patient. Because the resulting images are often analyzed in preparation for medical or dental procedures or to properly calibrate the imaging equipment, it is important that the images be as clear as possible. However, patient movement during the scan can cause errors or blurring in the images.

There are two general approaches to controlling the effects of patient motion. One approach is to physically restrain the patient. Physical restraints, however, are often not sufficient to prevent patient motion either because the patient can't stay still (e.g., a young child or due to a physical limitation) or because the operator does not properly use the patient restraint systems. In addition, some patient motion can occur even with careful patient positioning and restraint.

The other approach for controlling the effects of patient motion is to measure patient motion when it occurs and correct for it. Existing mechanisms for detecting patient movement include laser (optical) and ultrasonic (sound) based range finders or a set of stereoscopic cameras to detect patient position changes. However, the detectors, range finders, or cameras used in these systems add to the complexity and cost of the systems. For example, the rotating gantry in most scanning environments makes it difficult to place the detectors, range finders, or cameras in a location that isn't obstructed at some time during the gantry's rotation. In addition, mounting the hardware on the gantry itself increases the complexity of the detection process.

In computed tomography ("CT") imaging, reconstruction of the raw image data into final images relies on the fact that a particular physical structure changes its location from one projection image to the next in a mathematically-describable fashion. The equations describing the image-to-image trajectory of a structure's U and V positions through the sequence of projection images have parameters that describe the geometry of the gantry as well as parameters that represent the physical location of the structure in three-dimensional ("3D") space. If the parameters are fixed, the equations describe the trajectories exactly. However, if the parameters vary over the course of the scan (e.g., due to patient motion), the actual trajectories differ from the expected trajectories. The mathematical relationship between the measured positions of the structure and the expected positions of the structure is the basis for extraction of motion vectors representing the patient motion.

After motion is detected, multiple ways exists to correct the images for the detected motion. One way is to move the x-ray source detector to counteract the effect of the motion. This is the primary method used in cameras for image stabilization. The other way is to use information about the detected motion to correct image data after it is acquired. This can include deleting and reacquiring images corrupted by the detected movement. This approach, however, does not address continuous patient motion during the scan (i.e., motion that corrupts all or a majority of the images) and increases the amount of time needed to acquire the images. In addition, reacquisition of image data is not practical in some forms of single rotation scanning procedures.

Another way to correct for detected motion in images is to shift, zoom, and rotate the images in a manner that attempts to compensate for the detected motion and make the images appears as if no motion occurred. This approach can effectively address translational motion of a patient but it does not fully address rotational motion of the patient. For example, two points on a patient may be distinct, but after rotational movement of the patient, the points may appear as one point on the resulting image. Image shifting or zooming cannot, at least generally, correct for this situation.

Yet another way to correct detected motion is to warp the reconstruction grid as described in U.S. Patent Application No. 2004/0136590. Warping the reconstruction grid addresses deformable motion, such as motion that occurs during cardiac motion. Therefore, this approach uses information about detected motion to modify the reconstruction grid to make it account for the assumed deformation. While this approach can address a wide range of motion, forming the grids and matching the image data to the grids is complex. Therefore, this approach can be time-consuming and is subject to various types of artifacts.

Embodiments of the invention provide systems and methods for determining a six-component patient position (motion) vector for each projection image. One method includes taking the U and V positions of each of three or more x-ray fiducial markers on each projection image and determining the patient position shifts needed to explain the variations between the markers' actual locations and the markers' expected locations, if no patient motion occurs. Based on the variations, the method outputs a six-component vector that describes translational and rotational movement of the patient in the projection image. The method allows for the continuous tracking of patient motion during the entire scan with an accuracy of approximate 0.2 millimeter or better.

Embodiments of the invention also provide methods and systems for incorporating information about detected patient motion into the reconstruction process, which uses the information to compensate for the motion. One method includes taking a six-component position error vector (i.e., a patient motion vector) for each projection image and combining each vector with static gantry calibration information to create a projection matrix for each projection image. The projection matrix describes how each x-ray travels from the x-ray source, through the three-dimensional object, and to the two-dimensional x-ray detector. The reconstruction process uses the projection images and the projection matrices to reconstruct and correct the images for the detected patient motion.

In one particular embodiment, a method for determining patient motion in an image is provided. The method includes obtaining an image based on image data generated by a scanner during a scan. The image includes at least three markers assumed to be in a rigid or semi-rigid configuration, where each of the at least three markers has an actual measured position on a detector panel of the scanner in a first dimension and a second dimension. A reference three-dimensional position for each of the at least three markers is then determined by the electronic processing unit. The electronic processing unit then defines or sets up equations describing the relationship between the reference three-dimensional position and the actual measured positions of each of the at least three markers, geometric parameters of the scanner, and patient motion. Finally, the electronic processing unit numerically solves, the equations to derive a six-component motion vector describing patient motion for the image that accounts for differences between the reference three-dimensional position of each of the at least three markers and the actual measured positions for each of the at least three markers.

In another particular embodiment, a plurality of projection images are corrected and reconstructed based on detected patient motion. The method includes obtaining, at a computer, a plurality of projection images generated by a scanner. Each of the plurality of projection images includes at least three markers, and each of the at least three markers has a measured three-dimensional position and measured positions on a detector panel of the scanner in a first dimension and a second dimension. A position error vector for each of the plurality of projection images is determined by the electronic processing unit based on the at least three markers in each of the plurality of projection images. The position error vector defines patient motion in the projection image. Each position error vector for each of the plurality of projection images is combined with geometric parameters associated with the scanner to derive a projection matrix for each of the plurality of projection images. The plurality of projection images and the projection matrix for each of the plurality of projection images is provided or supplied to an image reconstructing process that generates reconstructed images corrected for patient motion.

Other aspects of the invention will become apparent by consideration of the detailed description and accompanying drawings.

DETAILED DESCRIPTION

Figure 1:
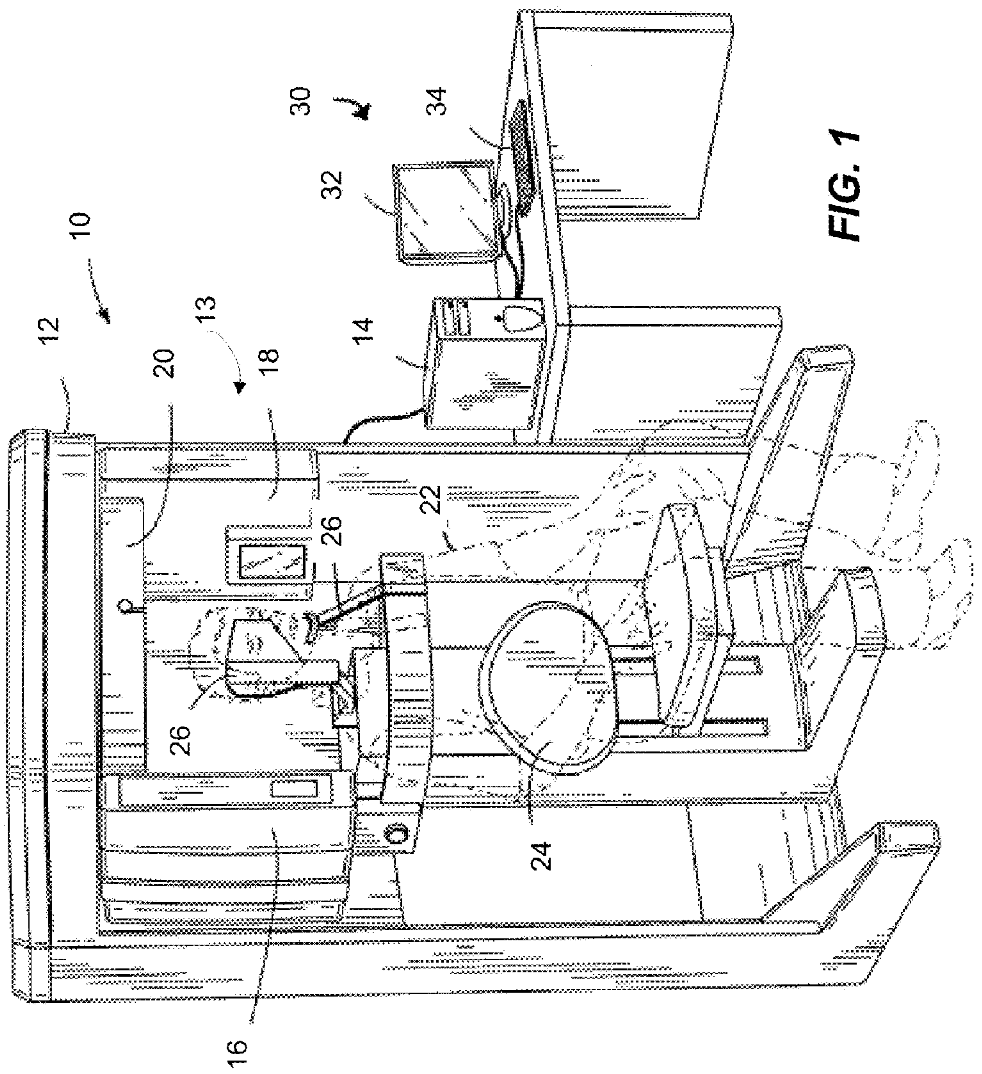
FIG. 1 illustrates a cone-beam computed tomography system according to one embodiment.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

It should also be noted that a plurality of hardware and software based devices, as well as a plurality of different structural components, may be utilized to implement the invention. Furthermore, and as described in subsequent paragraphs, the specific configurations illustrated in the drawings are intended to exemplify embodiments of the invention. Alternative configurations are possible.

Modern x-ray processes use one or more detectors rather than film. The detectors electronically detect and quantify the amount of (i.e., the intensity of) x-rays reaching the detector. Using the detectors, x-ray computed technology ("CT") systems were created that rotate an x-ray source around a patient and electronically detect the resulting x-rays with a single-wide strip of detector elements on the side of the patient opposite from the x-ray source. The combination of the x-ray source, the detectors, and the mechanical structure that allows rotation of the x-ray source is known as the "CT gantry." The data from the detectors is collected for all the different x-ray positions and then combined in a process known as reconstruction. The combined images represent a single, finite-width "slice" through the patient where the image's intensity at each point represents the x-ray density of the tissue at a particular physical location. The reconstruction process uses the fixed geometry of the CT gantry and the variable angle of the x-ray source-detector panel combination (i.e., θ) with respect to the patient to process the collected projection images.

Figure 2:
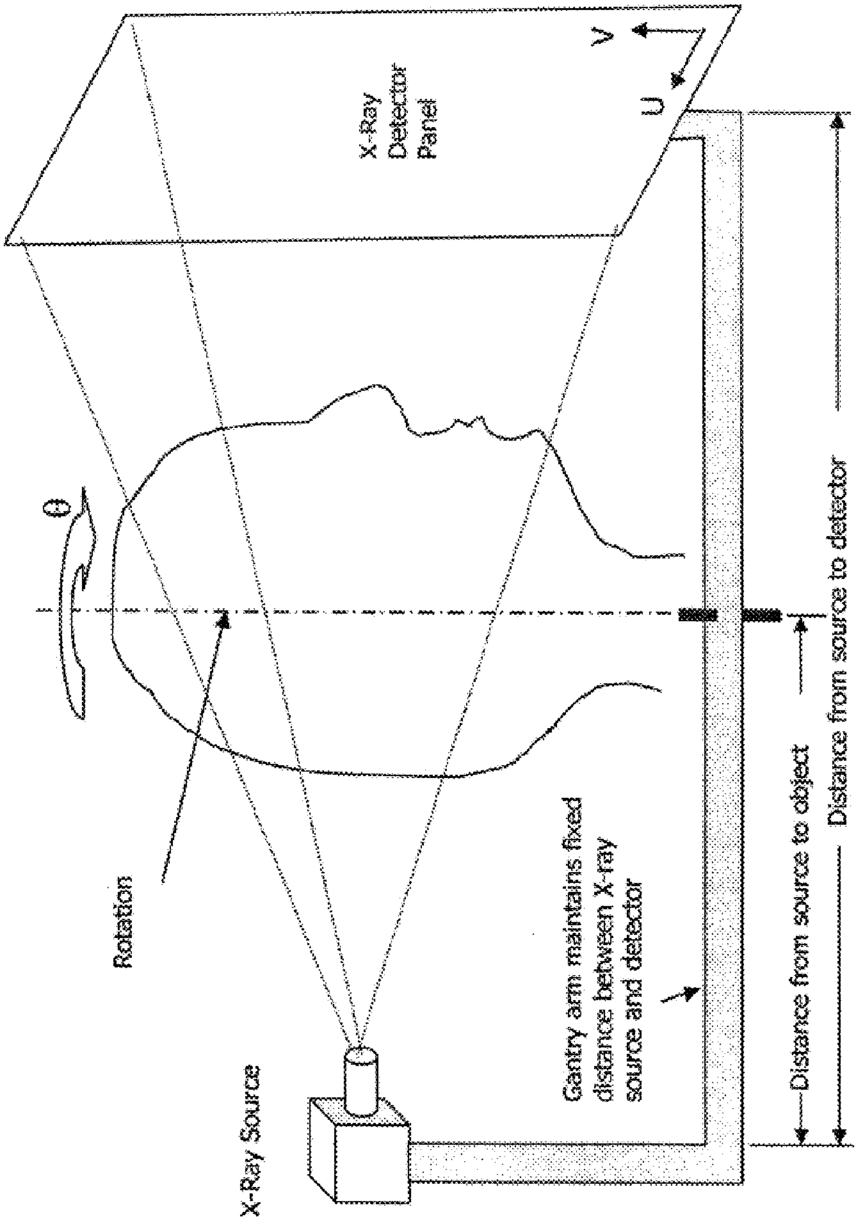
FIG. 2 schematically illustrates components of the cone-beam computed tomography system of FIG. 1 and their geometric relationships.

Multiple slices can be acquired by repeating the process while moving the patient, the x-ray source, or both between image acquisitions or scans. For example, moving the table supporting the patient while also rotating the x-ray source produces a "helix" instead of a slice of data. In addition, increasing the size or width of the detector strip or ring from a signal row of detectors to multiple rows (e.g., up to 256 rows) allows for more rapid acquisition of more data. Furthermore, replacing the detector strip with a larger two-dimensional detector acquires an entire detector panel image at each x-ray source position rather than just a single strip of data. The collections of these images, which can number 600 or more, are known as projection images. Each projection image represents an x-ray snap-shot of the patient from a different perspective or angle as the x-ray source and the detector are rotated in synchronization around the patient. Because of the cone-shaped x-ray beam needed to cover the two-dimensional detector, this type of CT imaging is known as cone-beam ("CB") CT imaging. FIG. 1 illustrates a CB CT imaging system 10 according to one embodiment, and FIG. 2 illustrates components of the CB CT imaging system 10 and their geometric relationships and parameters.

The CB CT imaging system 10 includes a scanner 12 and a computer 14. The scanner 12 includes a gantry 13 which includes an x-ray source 16 and a detector 18. The x-ray source 16 and the detector 18 are aligned across from each other on the rotating carrier 20, which moves the x-ray source 16 and the detector 18 around a patient 22. The patient 22 is supported by a seat 24. The imaging system 10 illustrated in FIG. 2 is a dental imaging system. Therefore, the patient 22 sits in the seat 24 and places his or her chin into a rest 26. The rest 26 holds the patient's head relatively still while the gantry 13 is rotated to complete a scan of the patient's head.

The scanner 12 outputs image data to the computer 14. The image data represents the intensity levels of x-rays detected by the detector 18 during the scan. The computer 14 is connected to a console 30, which includes a display 32 and one or more input and/or output devices, such as a keyboard 34. A user uses the console 30 to interact with the computer 14. For example, a user can use the console 30 to request images or other data from the computer 14. The computer 14 provides the requested information to the console 30, sends the information to a printer (not shown), and/or saves the information to a computer-readable memory module. Information is displayed on the display 32.

Figure 3:
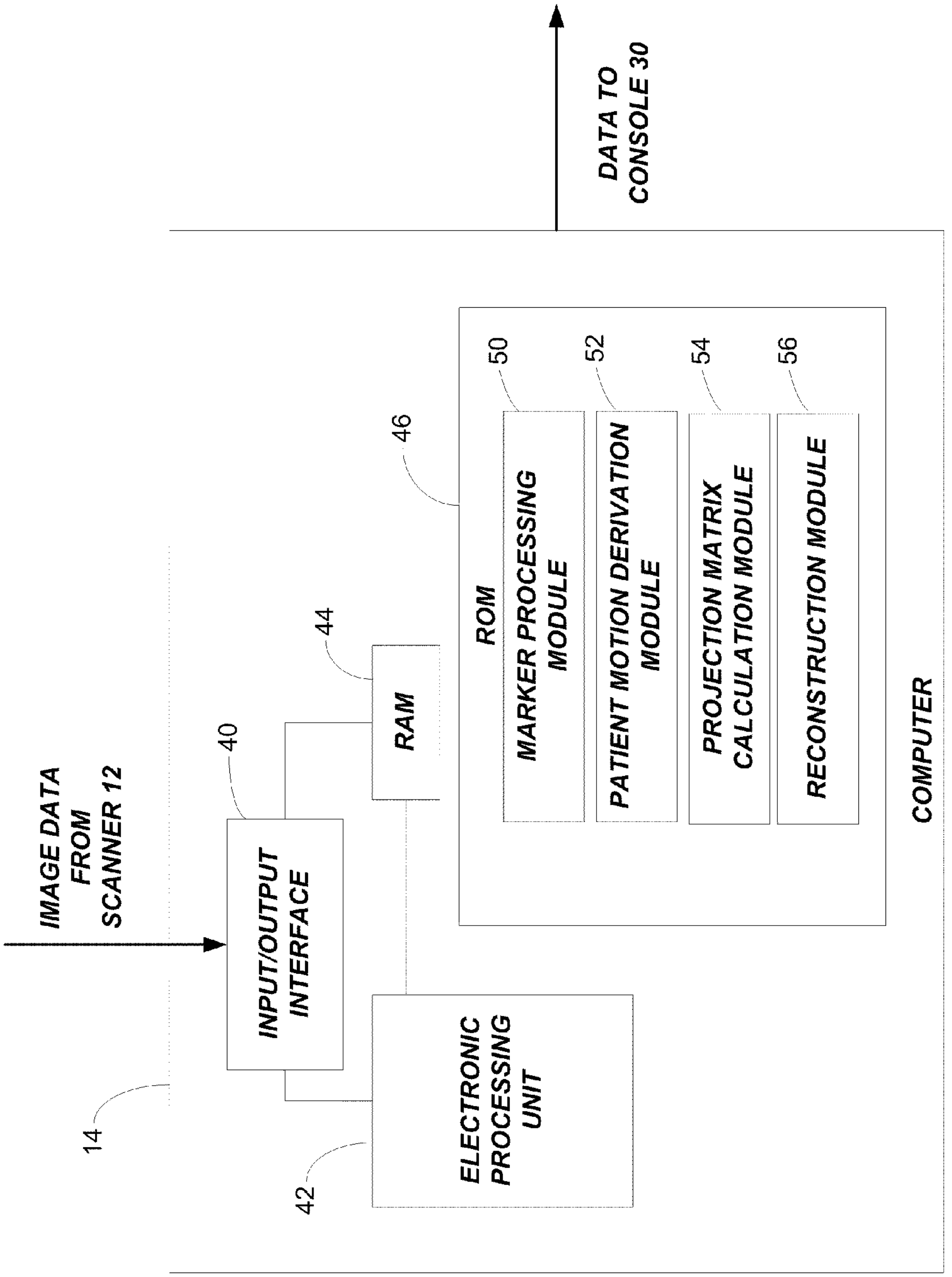
FIG. 3 schematically illustrates the computer of FIG. 1 according to one embodiment.

FIG. 3 schematically illustrates the computer 14 of FIG. 1 according to one embodiment of the invention. The computer 14 includes an input/output interface 40, an electronic processing unit ("EPU") 42, and one or more memory modules, such as a computer-readable disk accessible through a disk drive (not shown), a (random access memory ("RAM") module 44, a read-only memory ("ROM") module 46, or combinations thereof. The input/output interface 40 receives image data from the scanner 12 and provides the image data to the EPU 42.

In some embodiments, complete gantry rotation takes approximately eight to 40 seconds. During this time, a patient may move or the CT gantry may move unexpectedly, which causes blurring of the resulting images. Typical image resolution is on the order of 0.25 millimeter. Therefore, patient motion of this same order often causes image blurring and extensive patient movement can make the resulting images unacceptable for their intended clinical purpose. In addition, even when the blurring is not excessive, the blurring leads to a general decrease in image quality. For example, gantry vibrations can cause blurring and reduced image quality.

The computer 14 corrects the images for patient movement by tracking the movement of rigid or semi-rigid objects in the images. For example, in ideal conditions where there is no patient movement, imaged rigid objects change location in the two dimensions of the projection images in a well-defined way as the gantry rotates around the patient. Deviation between the expected locations of the objects in the image is caused by patient movement (or unexpected gantry movement). Therefore, by measuring a well-defined object's deviation from its expected locations, the amount of patient (and unexpected gantry) movement can be measured and corrected. In particular, as described below, if at least three objects are present in a sequence of images, the measured deviations of the objects from their expected locations can be combined to determine a patient motion vector, which can be applied to the images to correct for the patient movement.

To ensure that the desired number of well-defined rigid objects is present in the images, fiducial markers (e.g., three or more) are placed on a patient before a scan. The markers typically consist of lead or steel BBs, which are dense and prevent or limit x-rays from passing through. However, the markers may be made from other materials and constructed in other forms or shapes that are visible in a relatively high proportion of projection images generated during a scan. Each marker or multiple markers may be positioned between layers of adhesive and the adhesive can be applied to a patient to ensure that the markers do not move during the procedure. In addition, although more complicated, internal anatomical landmarks can be used as markers rather than externally-applied markers.

The markers are placed on a patient such that each field of view or image created by the CB CT imaging system includes at least three markers. For example, seven to nine markers may be placed on the patient to ensure that at least three markers are within each image, to decrease position measurement noise, and to allow statistical combination of the results. In some embodiments, the markers are evenly spaced on the patient to have a maximal spatial distribution about the patient and to avoid interfering with image interpretation.

Figure 4:
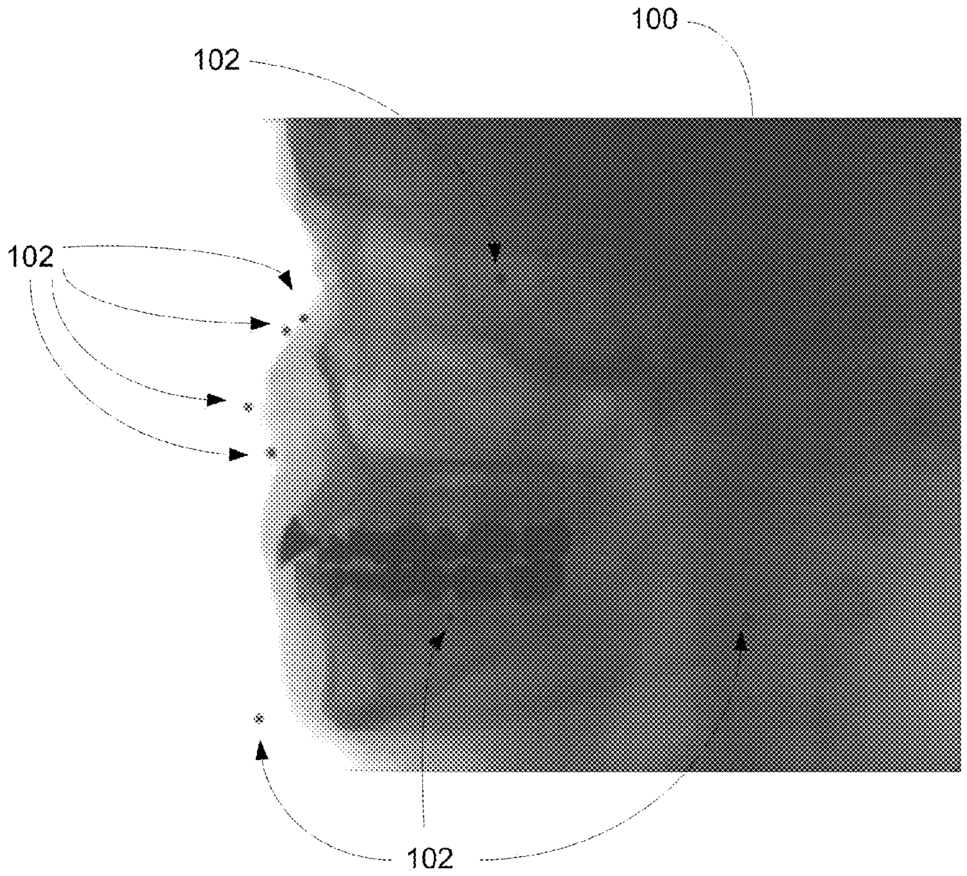
FIG. 4 illustrates an image including markers.

After the markers are placed on the patient, a scan is made of the patient, such as the patient's head and the resulting image data representing a sequence of projection images is transmitted to the computer 14. FIG. 4 illustrates an example projection image 100 that includes eight markers 102. It should be noted that the "markers 102" are representations of markers and not actual markers (i.e., the markers 102 are not actual bb's or similar devices.) Using the term marker to refer to both representations or images of markers and actual markers is consistent with ordinary grammatical syntax used by those of ordinary skill in the art. As a consequence, explicit distinctions between actual markers and representations of markers are not always made in the written description that follows.

Figure 5:
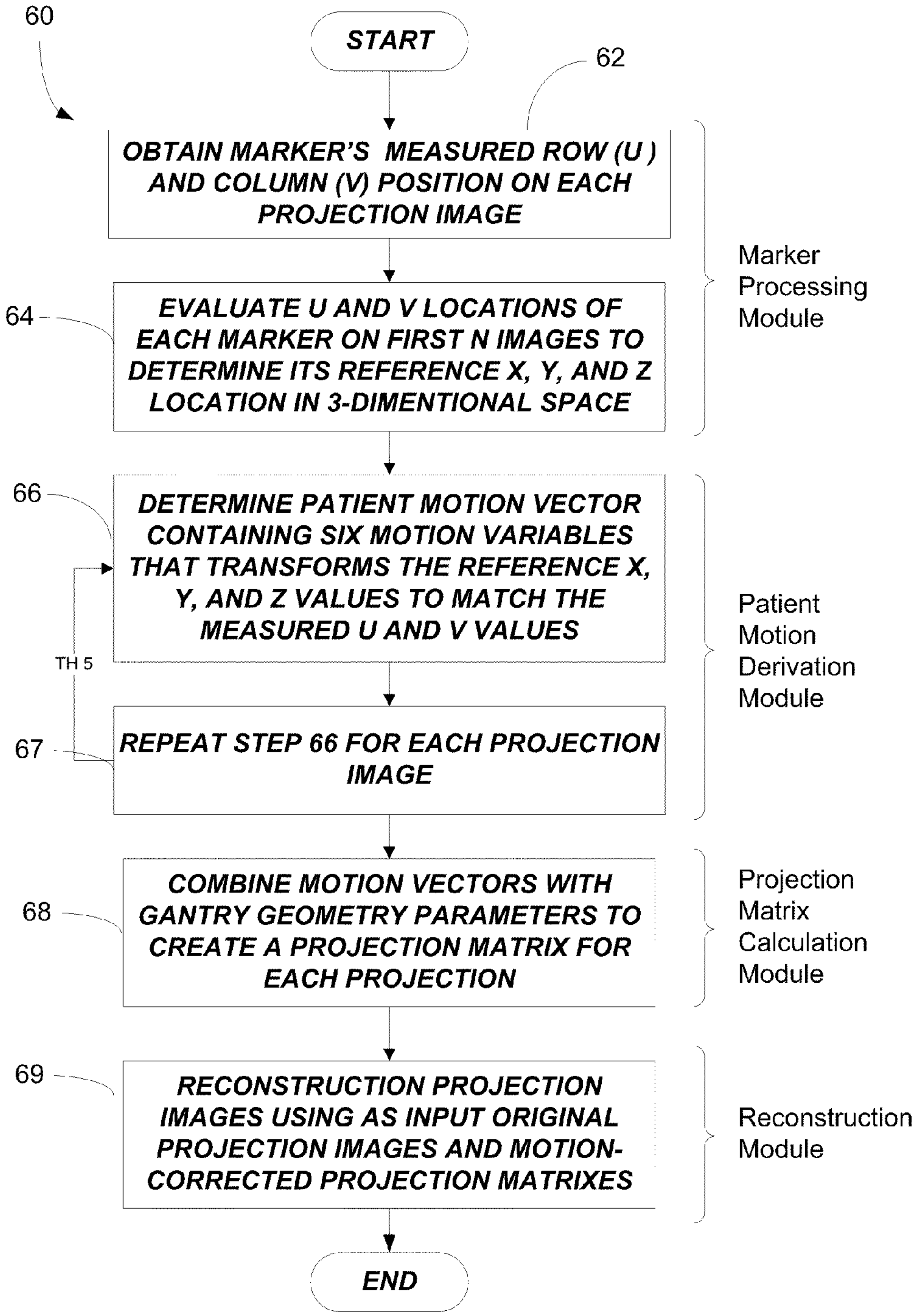
FIG. 5 is a flow chart illustrating a process of providing motion correction to reconstructed images according to one embodiment.

The EPU 42 receives the image data and processes the information by executing one or more applications or modules. The applications or modules are stored in a memory module, such as the ROM 46 or a computer-readable disk or medium accessible by the EPU 42 through a drive or external interface. As shown in FIG. 3, the memory module stores a marker processing module 50, a motion vector extraction module 52, a projection matrix calculation module 54, and a reconstruction module 56. FIG. 5 illustrates a method 60 that illustrates the flow of data through these four modules. As shown in FIG. 5, the EPU 42 retrieves projection images from the input/output interface 40 and executes the marker processing module 50 to identify marker points on each projection image, identify the vertical and horizontal position of each identified marker, assign each position and its dimensions to the appropriate physical marker, and use the image positional data to estimate a reference three-dimensional ("3D") physical location of each marker (steps 62 and 64). Various embodiments of this process of marker identification and processing are described in the co-pending application Ser. No. 12/626,197 entitled "MARKER IDENTIFICATION AND PROCESSING IN X-RAY IMAGES,"

Figure 6:
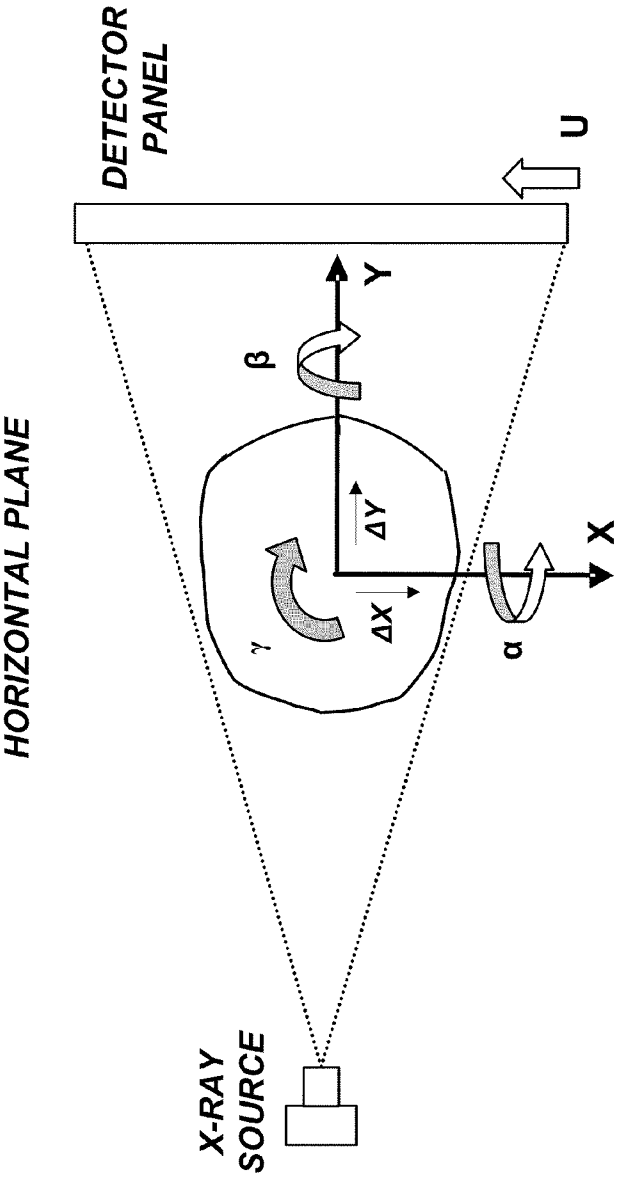
FIG. 6 graphically illustrates three types of rotational movement of a patient and two types of translational movement of a patient with respect to the horizontal plane of a detector panel.
Figure 7:
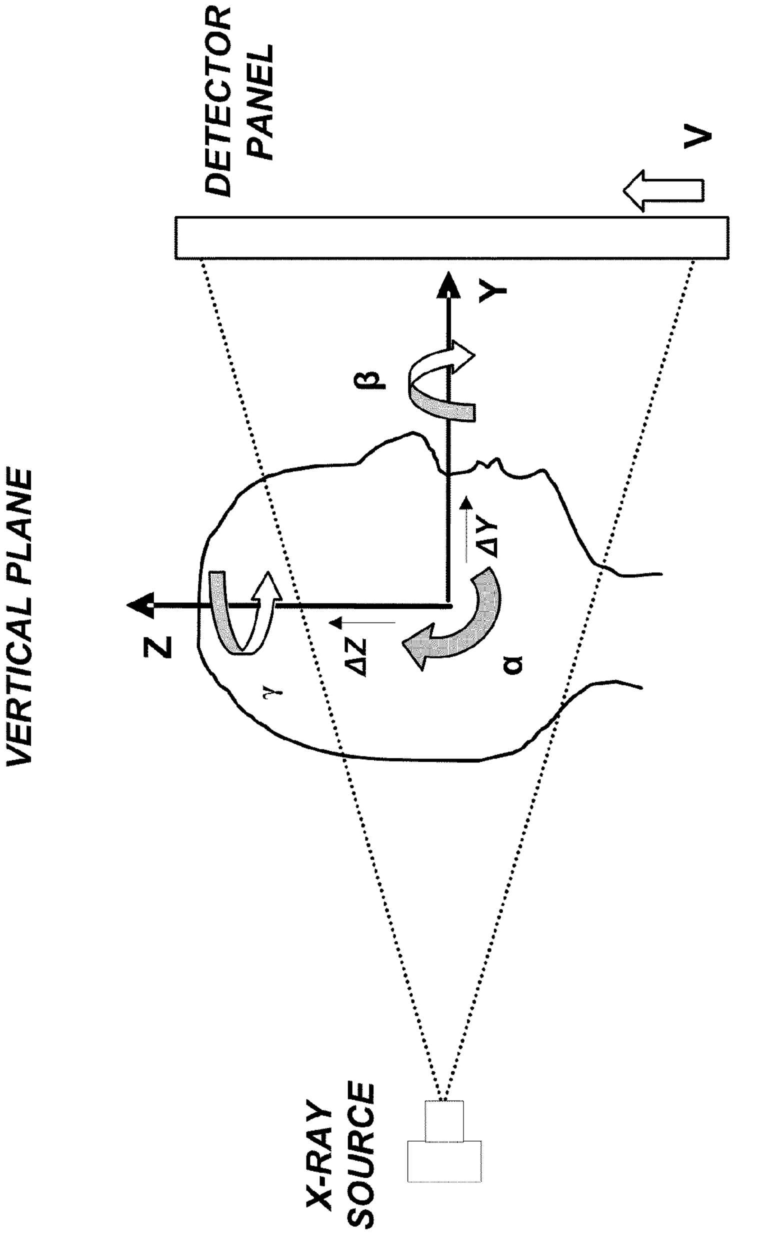
FIG. 7 graphically illustrates three types of rotational movement of a patient and two types of translational movement of a patient with respect to the vertical plane of a detector panel.
Figure 8:
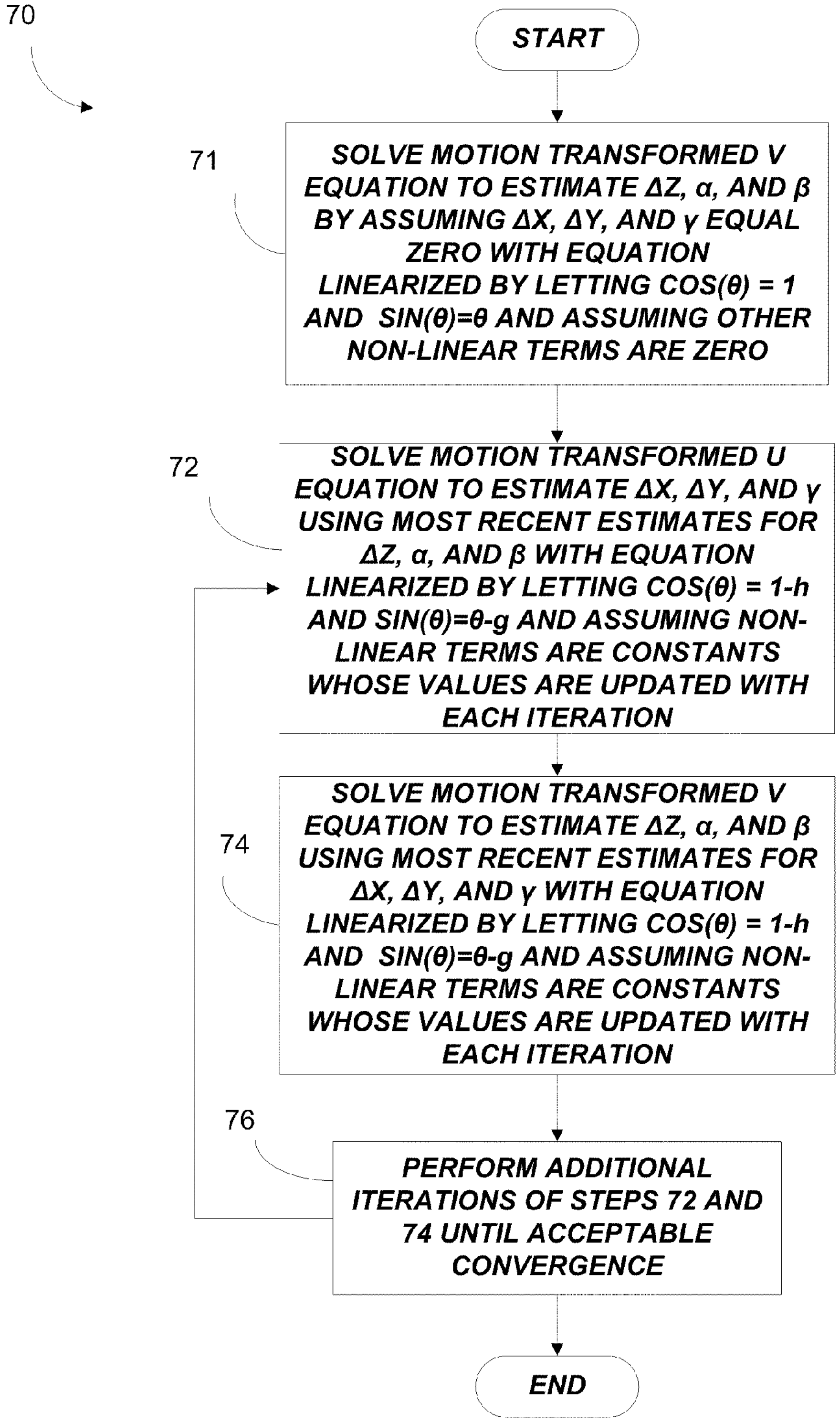
FIG. 8 is a flow chart illustrating a three-part process for determining a patient motion vector according to one embodiment.

As shown in FIG. 5, after the EPU 42 obtains the lists of marker points for each projection image, the EPU 42 executes the patient motion vector derivation module 52 to derive a six-component patient motion vector for each projection image (steps 66 and 67) (see FIGS. 6-8). The EPU 42 next executes the projection matrix calculation module 54 to determine a motion-corrected projection matrix for each projection image based on the six-component patient motion vectors and gantry geometry parameters (step 68) (see FIG. 9). Then the EPU 42 executes the reconstruction module 54 to create motion-correction volumetric images based on the motion-corrected projection matrices (step 69) (see FIG. 9). Portions of the method 60 are described below in detail.

Patient Motion Vector Derivation

As shown in FIG. 5, the first step of method 60 includes obtaining marker positional information for each marker in a projection image (step 62). Co-pending patent application Ser. No. 12/626,197 entitled "MARKER IDENTIFICATION AND PROCESSING IN X-RAY IMAGES," and discloses various embodiments for determining marker positional information for each marker in a projection image. The marker positional information includes the U (row) and V (column) location of each marker on each projection image. The U and V location for each marker provides the marker's 2D position relating to the detector panel of the scanner (i.e., $U_{M1}$, $V_{M1}$, $U_{M2}$, $V_{M2}$, $U_{M3}$, and $V_{M3}$). These measurements are the actual measured positions of the markers as detected in the presence of patient motion. As shown in FIGS. 6 and 7, a first dimension U is tangential to the circle of rotation of the CT gantry. The second dimension V is a plane parallel to the gantry's axis of rotation.

At step 64, the method 60 determines a reference 3D physical location (i.e., X, Y, and Z) for each marker based on the marker's U and V positional information. Motion of each marker is judged from the marker's reference position. The reference position is arbitrary and can be defined in various ways. In one embodiment, it is defined as the marker's position at the beginning of the scan. This position can be found in various ways, such as finding the X, Y, and Z coordinates that create a theoretical trajectory that best fits the observed trajectory of a marker. When three markers are used, the reference locations for the markers are defined by nine coordinate values (i.e., three markers times three coordinates each) labeled $X_1$, $Y_1$, $Z_1$, $X_2$, $Y_2$, $Z_2$, $X_3$, $Y_3$, and $Z_3$.

The following equations mathematically describe how a reference physical 3D point at location $X_i$, $Y_i$, and $Z_i$ is projected onto the 2D detector plane at a particular gantry rotation value $\theta_j$:

$$U_{ij} = \frac{DSD*(Y_i\cos\theta_j - X_i\sin\theta_j)}{(DSO + Y_i\sin\theta_j + X_i\cos\theta_j)} \quad \text{(equation 1)}$$

$$V_{ij} = \frac{DSD*Z_i}{(DSO + Y_i\sin\theta_j + X_i\cos\theta_j)} \quad \text{(equation 2)}$$

The subscript i represents the marker number and the subscript j represents the projection number. DSO is the distance from the x-ray source to the center of the gantry rotation, and DSD is the distance from the x-ray source to the detector panel. The variable $\theta_j$ is the current gantry angle of rotation. For example, $\theta_j$ is zero when the gantry source is directly behind the subject's head. The parameters DSO, DSD, and $\theta$ are generally illustrated in FIG. 2.

Next at step 66, the method 60 determines a patient motion vector containing six motion variables for a particular projection image (i.e., $\Delta X$, $\Delta Y$, $\Delta Z$, $\alpha$, $\beta$, and $\gamma$). In general, this step determines a six-component motion vector for each projection image that describes the overall motion of the scanned object (e.g., the patient's head), when the object is treated is a rigid body. Each motion vector accounts for the differences between the observed positions (U and V) of each marker in the projection image and the predicted location of each marker assuming ideal gantry motion and known, fixed (e.g., no motion) physical X, Y, and Z reference locations for each marker.

For example, at this step the computer receives as input an object list for each marker that lists positional information for the marker in each projection image. If there are at least three markers in each projection image, the computer outputs a six-component motion vector for each projection image that represents the detected motion for that image based on the marker object lists for the markers included in the image. Three of the six components represent the translational shift or motion of the patient in the X, Y, and Z dimensions (i.e., variables $\Delta X$, $\Delta Y$, and $\Delta Z$) and the other three components represent the rotational shift or motion of the patient about the X, Y, and Z axes (i.e., variables $\alpha$, $\beta$, and $\gamma$).

As shown in FIG. 5, a patient motion vector is determined for each projection image independent of the other projection images (step 67). Therefore, the final result of steps 66 and 67 is a set of motion vectors including a number of vectors equal to the number of projection images. For example, a 600-projection image study would produce a motion vector set with 600 independent vectors. The actual number of vectors produced, however, may be less if one or more projection images do not include three or more markers, which prevents the method 60 from deriving motion information.

It should be noted that in some embodiments, the motion vectors are estimates of exact motion vectors for a projection image. For example, during a scan each marker undergoes a different change in its X, Y, and Z position. The method 60 uses the different movements of each marker in each projection image to create the six-component motion vector. If there are three markers, an exact answer or motion vector can be determined using the six equations (i.e., U and V equations for each for the three markers) and the six unknowns (i.e., the components of the motion vector). However, if there are more than three markers in an image, there are more equations than unknowns and the problem is overspecified. In addition, marker measurements cannot always be measured exactly due noise. Therefore, because the problem is overspecified and there is measurement noise, a motion vector determined by method 60 is an estimate of the exact motion vector for a particular projection image.

Returning to step 66, various equations and formulations can be defined to determine the patient motion vector. For example, if there is no patient motion, $X_i$, $Y_i$, and $Z_i$ for a particular marker are constant for all projection images, which implies that U and V vary only because of the changing $\theta$. However, when there is patient motion, $X_i$, $Y_i$, and $Z_i$ vary due to the localized effect of the motion. Therefore, in the presence of patient motion, each coordinate is more properly represented by:

$$X_i = X_{i\,ref} + x_{ij} \qquad Y_i = Y_{i\,ref} + y_{ij} \qquad Z_i = Z_{i\,ref} + z_{ij}$$

Where $x_{ij}$, $y_{ij}$, and $z_{ij}$ represent the difference in a particular marker's i position from its reference location at a particular projection j associated with patient motion. Substituting these values into equations 1 and 2 shown above yields the following revised equations:

$$U_{MEASij} = \frac{DSD*((Y_{ref\,i}+y_{ij})*\cos\theta_j-(X_{ref\,i}+x_{ij})*\sin\theta_j)}{(DSO+(X_{ref\,i}+x_{ij})*\cos\theta_j+(Y_{ref\,i}+y_{ij})*\sin\theta_j)} \quad \text{(equation 3)}$$

$$V_{MEASij} = \frac{DSD*(Z_{ref\,i}+z_{ij})}{(DSO+(X_{ref\,i}+x_{ij})*\cos\theta_j+(Y_{ref\,i}+y_{ij})*\sin\theta_j)} \quad \text{(equation 4)}$$

For the case when three markers are used, at a particular $\theta_j$, there are six equations (U and V for each of three markers) and nine unknowns ($x_{ij}$, $y_{ij}$, and $z_{ij}$ for each of the three markers) which, without additional information, cannot be solved.

However, if a constraint is added that assumes that all the markers lie fixed within or on a rigid object, the motion of any particular marker can be completely described by its reference location and the motion of the entire object as provided by the six transformation parameters (i.e., motion vector components), ΔX, ΔY, ΔZ, α, β, and γ. The variables ΔX, ΔY, ΔZ define translational motion of the patient in the projection image, and the variables α, β, and γ represent the rotational motion of the patient in the projection image, as shown in FIGS. 6 and 7. Therefore, by adding the rigid object constraint, there are now only six unknowns and six equations, which makes the problem solvable.

To further simplify the equations and formulations, the frame of reference for the objects can be changed from a fixed (i.e., to the earth) frame of reference to a rotating gantry frame of reference. The fixed-to-rotation frame transformation can be combined with the patient motion transformation to provide an overall motion transformation. The following matrix provides this combination:

$$|\Gamma_{transformed}|=|A_{overall}||\Gamma_{ref}|=|\theta_{rotation}||A_{patient\_motion}||\Gamma_{ref}| \quad \text{(equation 5)}$$

Where $|\Gamma|$ is the position vector of an object containing the components X, Y, and Z and $|A_{patient\_motion}$ is the motion transformation matrix that contains components associated with the ΔX, ΔY, ΔZ, α, β, and γ translations and rotations and $|\theta_{rotation}|$ is the rotation matrix associated with the gantry's rotation for a particular projection image. This implies that an alternative formulation of equations 3 and 4 above would be:

$$U_{MEASij} = \frac{DSD*Y_{transformed\ j}}{DSO+X_{transformed}} \quad \text{(equation 6)}$$

$$v_{MEASij} = \frac{DSD*Z_{transformed\ j}}{DSO+X_{transformed}} \quad \text{(equation 7)}$$

where:

$$X_{transformed\ j} = f_1(X_{ref\,i}, Y_{ref\,i}, Z_{ref\,i}, \Delta X, \Delta Y, \Delta Z, \alpha, \beta, \gamma, \theta) \quad \text{(equation 8)}$$

$$Y_{transformed\ j} = f_2(X_{ref\,i}, Y_{ref\,i}, Z_{ref\,i}, \Delta X, \Delta Y, \Delta Z, \alpha, \beta, \gamma, \theta) \quad \text{(equation 9)}$$

$$Z_{transformed\ j} = f_3(X_{ref\,i}, Y_{ref\,i}, Z_{ref\,i}, \Delta X, \Delta Y, \Delta Z, \alpha, \beta, \gamma, \theta) \quad \text{(equation 10)}$$

and $f_1$, $f_2$, and $f_3$ are defined by the transformation equation (i.e., equation 5) above.

Therefore, given the "fixed" parameters DSD, DSO, $X_{ref1}$, $Y_{ref1}$, $Z_{ref1}$, $X_{ref2}$, $Y_{ref2}$, $Z_{ref2}$, $X_{ref3}$, $Y_{re3}$, and $Z_{ref3}$ and the measurements of $U_{MEAS1}$, $V_{MEAS1}$, $U_{MEAS2}$, $V_{MEAS2}$, $U_{MEAS3}$, and $V_{MEAS3}$ at a particular θ, the method 60 uses equations 5, 6, and 7 to find the motion parameters ΔX, ΔY, ΔZ, α, β, and γ at this θ and for every other θ in the sequence of projection images.

It should be noted that equations 6 and 7 illustrated are inherently non-linear. The motion transformation represented by equations 5, 8, 9 and 10 have sine and cosine components associated with the rotational parts of the transformation. Also, the simultaneous solution of equations 6 and 7 represents a non-linear operation because of the division inherent in each. All of these factors imply that an exact solution cannot be found and an iterative solution would be prohibitively time-consuming. However, by employing a few simplifications, a practical solution can be determined. FIG. 8 is a flow chart illustrating a three-part method 70 for determining a patient motion vector according to one embodiment of the invention. The method 70 is performed by the EPU 42 of the computer 14 when the EPU 42 executes the patient motion vector derivation module. The method 70 employs two simplifications, both based on the premise that actual patient motion is relatively small compared to gantry motion.

The first simplification linearizes the equations by applying a Taylor Series expansion to the sines and cosines in the rotational transformations and considers only the first term in each. Effectively, this means cos(x) is replaced with 1 and sin(x) is replaced with x. This assumption is valid for small values of rotational components. However, as described below, the method 70 can employ an iterative approach that allows this restriction to be relaxed.

The second simplification takes advantage of the fact that the V equation is more sensitive to changes in α, β, and ΔZ and less sensitive to changes in ΔX, ΔY, and γ. Conversely, the U equation is more sensitive to changes in ΔX, ΔY, and γ and less sensitive to changes in α, β, and ΔZ. This means that, for small amounts of motion, the overall problem can be simplified by breaking the problem into two parts. In particular, first, the simultaneous linearized V equations for α, β, and ΔZ can be solved, and then the simultaneous linearized U equations for ΔX, ΔY, and γ can be solved using as constants the previously found values for α, β, and ΔZ using the V equation.

As noted above, using iterations can improve the solution's level of accuracy. The iteration (step 76) involves repeatedly solving the U equations (step 72) and the V equations (step 74). Within each equation's solution, there are two components to how iteration increases accuracy. First, each solution of V uses the most recent, increasingly accurate, values for ΔX, ΔY, and γ found from the previous solution of U. Likewise each solution of U uses the most recent values of α, β, and ΔZ found from the previous solution of V (step 74). The second component is the use of residuals. To do this, the higher order (non-linear components) of the U and V equations are considered to be pseudo-constants to allow the linear formulation. This assumption can be made because patient motion can be consider small compared to normal gantry motion. After each solution of any of the U or V equations (steps 71, 72, or 74), the pseudo-constants are updated to their increasingly accurate values. For the first solution of V (step 71), no information exists before the solution is performed to set values for either the pseudo-constants or ΔX, ΔY, and γ. Before performing this step, these parameters are set to zero"

Further details of solving the V equation and the U equation are provided below.

Solving the V Equation

To solve the V equation, note that the component α is defined as rotation about the X axis, β is defined as rotation about the Y axis, and γ is defined as rotation about the Z axis. Accordingly, the matrix form of the rotation represented by α is the following:

$$rot\alpha = \begin{bmatrix} 1 & 0 & 0 \\ 0 & \cos(\alpha) & -\sin(\alpha) \\ 0 & \sin(\alpha) & \cos(\alpha) \end{bmatrix}$$

Applying a Taylor expansion to this matrix linearizes the sines and cosines in the matrix.

$$\cos(\alpha) = 1 - \frac{\alpha^2}{2!} + \frac{\alpha^4}{4!} + \ldots$$

$$\sin(\alpha) = \alpha - \frac{\alpha^3}{3!} + \frac{\alpha^5}{5!} + \ldots$$

For small angles, the first terms, 1 and α, represent reasonable approximations of cos(α) and sin(α) respectively. Alternatively, the accuracy can be improved by correcting the first term with an estimate of the higher terms. With no prior knowledge, however, the best estimate for these higher order terms is zero. But, once the linear approximations for sin(α) and cos(α) are used to find and approximate value for α, this value of α can be used to improve the approximation for the higher order terms. In other words, the representations for cos(α) and sin(α) can be each be given by an expression containing two terms: a linear (in α) term and a non-linear residual, which can be considered a constant during any iteration.

For example, the following provides mathematical representations for cos(α) and sin(α) where cos(α) has been replaced by c1 and sin(α) has been replaced by s1 to improve conciseness.

$$\cos(\alpha)=c1=1-h1$$

$$h1=1-c1$$

$$\sin(\alpha)=s1=a1-g1$$

$$g1=a1-s1$$

Where h1 represents the residual cos(α) and g1 represents the residual for sin(α). The suffix number 1 is used to indicate the rotation α.

Using the suffix number 2 to represent the rotation β, the suffix number 3 to represent the rotation γ, and the suffix number 4 to represent the gantry rotation θ, the following matrices define each of the rotations of interest.

$$rot\alpha = \begin{bmatrix} 1 & 0 & 0 \\ 0 & 1-h1 & -a1+g1 \\ 0 & a1-g1 & 1-h1 \end{bmatrix} \quad \text{(equation 11)}$$

$$rot\beta = \begin{bmatrix} 1-h2 & 0 & -a2+g2 \\ 0 & 1 & 0 \\ a2-g2 & 0 & 1-h2 \end{bmatrix} \quad \text{(equation 12)}$$

$$rot\gamma = \begin{bmatrix} c3 & -s3 & 0 \\ s3 & c3 & 0 \\ 0 & 0 & 1 \end{bmatrix} \quad \text{(equation 13)}$$

$$rot\theta = \begin{bmatrix} c4 & -s4 & 0 \\ s4 & c4 & 0 \\ 0 & 0 & 1 \end{bmatrix} \quad \text{(equation 14)}$$

Note that a1=α and a2=β and have been broken out since these are two variables that need to be solved. In contrast, γ and θ have not been broken out since each of these variables is considered a fixed parameter during the solution of the V equations.

For the translation component of the motion, the following vector represents the 3-component reference position of a particular marker.

$$position_{original} = \begin{bmatrix} X0 \\ Y0 \\ Z0 \end{bmatrix}$$

The transformation of a marker from one position to another can involve up to 3 positional shifts (translations) and 3 rotation shifts. The exact order of these shifts and translations is arbitrary but must be defined for a particular formulation. For example, the motion transformation can be defined as first involving a three component translation shift followed in succession by a α rotation, a β rotation, a γ rotation, and finally a θ (gantry) rotation. This definition is used in the following derivations but other definitions would be equally suitable.

New X, Y, and Z positions for a particular marker can be defined by simply adding the motion displacement (XD, YD, or ZD) to the marker's corresponding reference position. However, within this V equation solution, the X and Y positions are assumed constant and can be simplified by using two symbols, XS and YS. Using these symbols, the following vector represents a marker's translated position (position after translational movement but rotations are applied).

$$position_{translated} = \begin{bmatrix} X0+XD \\ Y0+YD \\ Z0+ZD \end{bmatrix} = \begin{bmatrix} XS \\ YS \\ Z0+ZD \end{bmatrix}$$

After rotations are applied, the marker is now at its full motion-displaced location. This new position is called the transformed position vector and is given in the following equation.

$$\begin{bmatrix} X_{transformed} \\ Z_{transformed} \\ Z_{transformed} \end{bmatrix} = rot\theta \times rot\gamma \times rot\beta \times rot\alpha \times \begin{bmatrix} XS \\ YS \\ Z0+ZD \end{bmatrix} \quad \text{(equation 15)}$$

At this point, the V equation can be solved. For example, the V equation was given above as equation 6 and is repeated here as equation 16:

$$V = \frac{DSD * Z_{transformed}}{DSO - X_{transformed}} \quad \text{(equation 16)}$$

Equation 16 represents the relationship between V and the motion-transformed marker location for one particular marker. If equation 16 is combined with equations 11, 12, 13, 14, and 15, the resulting equation contains the three sought after variables: a1, a2, and ZD (corresponding to α, β, and ΔZ).

$$
\begin{aligned}
0 = {} & -DSD*YS*g1 - DSD*YS*h2*a1 + \\
& DSD*h2*h1*Z0 + V1*c4*c3*g2*Z0 + V1*XS*c4*c3 - \\
& V1*YS*c4*s3 + DSD*h2*h1*ZD - V1*YS*s4*c3 + \\
& V1*s4*s3*a2*ZD - V1*DSO - DSD*h1*Z0 - DSD*h2*ZD + \\
& V1*YS*s4*s3*a2*a1 - V1*XS*s4*s3 - DSD*XS*g2 + \\
& DSD*YS*a1 - DSD*h2*Z0 + DSD*XS*a2 - DSD*h1*ZD + \\
& DSD*YS*h2*g1 + V1*c4*c3*g2*ZD + V1*YS*a2*c4*c3*g1 - \\
& V1*s4*s3*g2*ZD - V1*s4*c3*g1*ZD + \\
& V1*YS*c4*c3*g2*a1 - V1*YS*a2*s4*s3*g1 - \\
& V1*YS*s4*s3*g2*a1 - V1*YS*c4*c3*g2*g1 + \\
& DSD*Z0 + DSD*ZD - V1*c4*s3*g1*ZD - \\
& V1*s4*c3*g1*Z0 + V1*YS*s4*s3*g2*g1 - \\
& V1*s4*s3*g2*Z0 - V1*c4*s3*g1*Z0 + V1*c4*s3*a1*Z0 + \\
& V1*c4*s3*a1*ZD + V1*s4*c3*a1*Z0 + \\
& V1*s4*c3*a1*ZD - V1*c4*c3*g2*h1*Z0 - \\
& V1*s4*s3*a2*h1*Z0 - V1*s4*s3*a2*h1*ZD + \\
& V1*XS*s4*s3*h2 - V1*XS*c4*c3*h2 + V1*YS*c4*s3*h1 - \\
& V1*c4*c3*a2*Z0 - V1*c4*c3*a2*ZD + \\
& V1*s4*s3*a2*Z0 - V1*YS*c4*c3*a2*a1 - \\
& V1*c4*c3*g2*h1*ZD + V1*s4*s3*g2*h1*Z0 + \\
& V1*s4*s3*g2*h1*ZD + V1*YS*s4*c3*h1 + \\
& V1*c4*c3*a2*h1*Z0 + V1*c4*c3*a2*h1*ZD
\end{aligned}
$$

One such equation exists for each marker.

In order to solve the above equation, it must be placed in the form:

$$a1*A+a2*B+ZD*C+D=0 \quad \text{(equation 17)}$$

This is done by grouping together those sub-expressions that contain only one of the three variables, a1, a2, or ZD in a state no higher than the first power and that don't contain any of the sine or cosine residuals, g1, g2, h2, or h2. These three groups of sub expressions become the coefficients, A, B, and C. All other terms are gathered together into the "constant" term, D.

Once this sorting is done, a system of m linear equations of the form illustrated by equation 17 (with one equation for each marker) is obtained. If there are 3 markers, the solution is found by a simple matrix inversion. If more that three markers exist, the solution can be found using a Singular Value Decomposition ("SVD"). SVD effectively provides the values for a1, a2, and ZD that minimize the squared error associated with each equation.

For the first iteration, the sub-expressions making up D that include higher order combinations of a1, a2, and/or ZD or contain the sine or cosine residuals, g1, g2, or h1, or h2 are assumed to be zero. However, in subsequent iterations, improved estimates for this higher order terms can be provided.

Solving the U Equation

The solution for the variables, XD, YD, and a3, representing ΔX, ΔY, and γ, respectively, can be accomplished in a totally analogous manner as solving the V equation using the equation the provides the U position given a particular transformed X and Y position:

$$U = \frac{DSD*Y_{transformed}}{DSO - X_{transformed}}$$

In this case, equation 4 remains the same and equations 11, 12, 13, and 15 become:

$$rot\alpha = \begin{bmatrix} 1 & 0 & 0 \\ 0 & c1 & -s1 \\ 0 & s1 & c1 \end{bmatrix} \quad \text{(equation 18)}$$

$$rot\beta = \begin{bmatrix} c2 & 0 & -s2 \\ 0 & 1 & 0 \\ s2 & 0 & c2 \end{bmatrix} \quad \text{(equation 19)}$$

$$rot\gamma = \begin{bmatrix} 1-h3 & -s3+g3 & 0 \\ s3-g3 & 1-h3 & 0 \\ 0 & 0 & 1 \end{bmatrix} \quad \text{(equation 20)}$$

$$\begin{bmatrix} X_{transformed} \\ Z_{transformed} \\ Z_{transformed} \end{bmatrix} = rot\theta \times rot\gamma \times rot\beta \times rot\alpha \times \begin{bmatrix} X0+XD \\ Y0+YD \\ ZS \end{bmatrix} \quad \text{(equation 21)}$$

After the substitutions, the resulting equations must be sorted to provide an equation of the following form:

$$XD*E+YD*F+a3*G+H=0 \quad \text{(equation 22)}$$

Again, one of these equations will exist for each marker. The equations can be solved either with a matrix inversion or with Singular Value Decomposition.

While equations 17 and 22 can be solved in either order, the preferred implementation is to first solve equation 17, then equation 22, and then iterate through these two equations two or more times. Two iterations have been found to provide reasonable, usable estimates for motion, but having more iterations is preferred. Accuracy (better than six decimal places) can be obtained with only five iterations. Because each iteration involves inverting only 3×N matrices when N is typically less than 10, the overall solution can be performed rapidly.

A sample implementation of the above methods for solving the V and U equations, in the Matlab programming language, according to one embodiment of the invention is provided in Appendix A. The un-compiled Matlab code computation time for 24 markers and 5 iterations at each of 300 projections performed on a Intel Core 2 U7600 CPU was approximately 0.2 seconds, which represents an approximate solution time for each projection of 7 milliseconds. Most of the computation time is associated with Singular Value Decomposition matrix solution.

Returning to FIG. 5, after the six-component motion vector is determined for the sequence of projection images, the EPU 42 retrieves and executes the projection matrix calculation module 54 and the reconstruction module 56 at steps 68 and 69 to create corrected and reconstructed projection images. These steps are described in more details in the next section (see FIG. 9).

It should be noted, that in the above description of method 70, it was assumed that the gantry rotates about the patient in a perfect manner (i.e., there is no gantry motion other than the desired rotation). However, this condition may be relaxed and the method 70 may be modified to account for unplanned gantry motion. The method 70 may also be modified to work with more complex gantry geometries and rotations.

Also, in method 70, the markers do not need to have a fixed relationship to each other when placed on the patient. The relationship between the markers can be derived from piece-wise analysis of marker trajectory behavior as long as the patient motion is not too severe. However, in some embodiments, once placed, the markers need to maintain a fixed relationship with each other. This means method 70 works well on a rigid body, such as the human head. However, if more markers are employed, the method 70 may also be used for less rigid bodies. For example, as long as three (or more) markers have a fixed relationship for a particular region, more than one region can be evaluated. This concept is useful for separately evaluating motion of the mandible and maxilla in the head when the jaw is moving. In addition, if three markers are fixed on a rigid frame, the motion of the frame can be evaluated. This approach may be useful for anatomically deformable motion, such as respiration.

In addition, marker placement for the method 70 is generally important as measurement errors due to marker placement affects the accuracy of the results of the method 70. For example, the larger the separation between the markers, the smaller the measurement error will be. In one embodiment, the markers are placed 180 degrees around the patient's head, which provides a motion vector component detection accuracy of approximately 0.2 millimeters or better.

Because the method 70 produces independent estimates of motion for each projection image, the method provides additional flexibility. First, if less then three markers are detected in a particular projection image, the method can interpolate the motion in the projection image from adjacent projection images. Second, the method can use the data related to each projection image to filter adjacent projection results and further improve the process's correction effectiveness.

Furthermore, because the method 70 uses imaging data to extract motion information, the detected motion consists both of patient movement and uncorrected or unplanned gantry movement. The information about the unplanned gantry movement may be used to dynamically correct gantry motion. For example, using the method 70, corrections may be made during a patient scan (e.g., if the patient is instrumented) or as part of a calibration process in between patient scans using a multi-marker phantom.

Image Correction and Reconstruction

Figure 9:
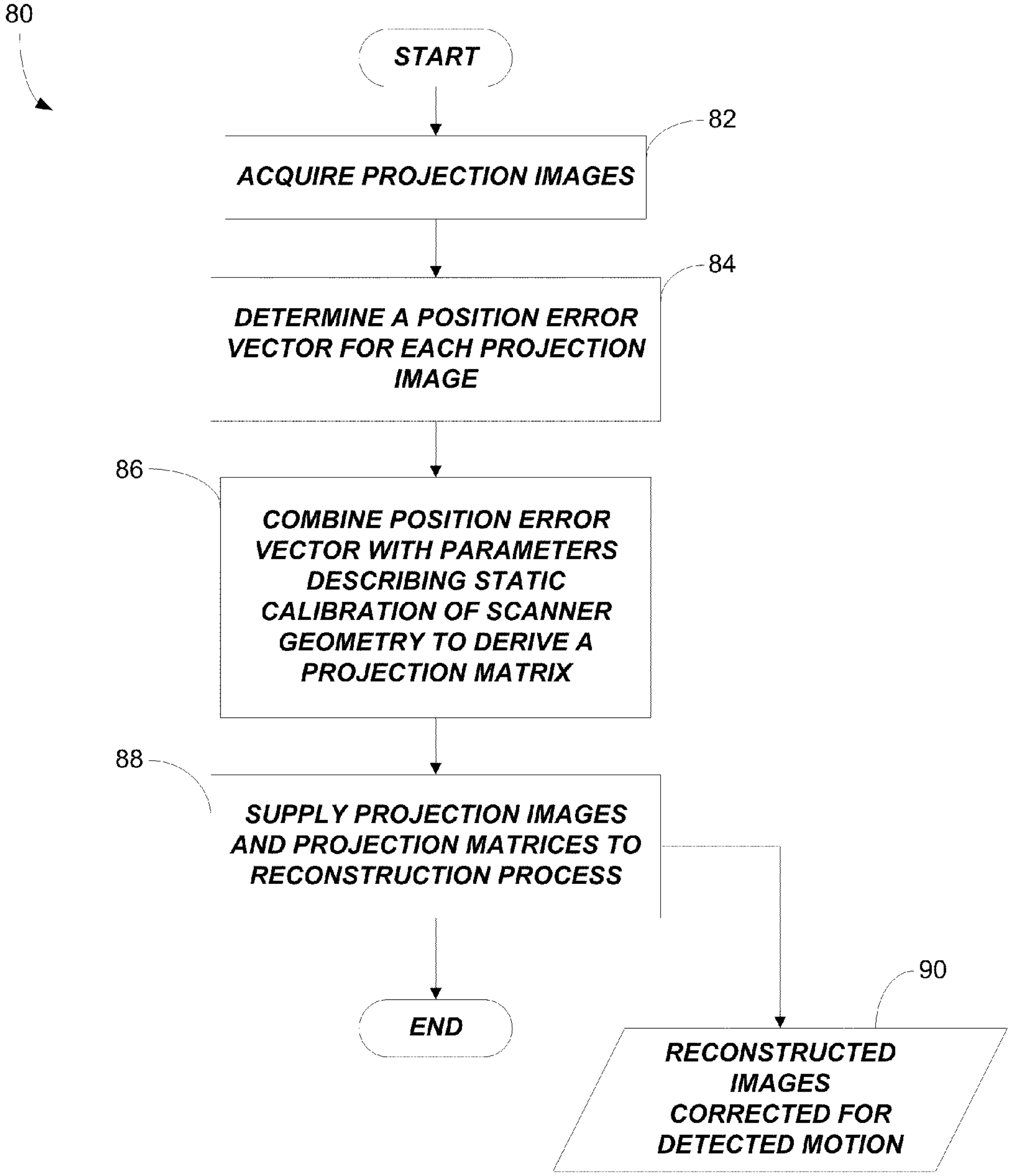
FIG. 9 is a flow chart illustrating an image correction method according to one embodiment.

Returning to FIG. 5, after motion is detected in the projection images, the computer 14 reconstructs and corrects the images based on the detected motion (steps 68 and 69). FIG. 9 illustrates a method 80 that performs these steps according to one embodiment of the invention. The image correction method 80 is performed by the EPU 42 of the computer 14 when the EPU 42 executes the projection matrix calculation module 54 and the reconstruction module 56.

In general, the method 80 corrects the projection images for motion by incorporating information about the detected motion into the reconstruction process. The method 80 addresses non-deformable motion detected in the images, which is specified for each projection image by a six-component vector (i.e., a patient motion vector). As described above, the six-component vector includes three parameters for X, Y, and Z translational motion (i.e., ΔX, ΔY, and ΔZ) and three parameters for rotational motion about the X, Y, and Z axes (i.e., α, β, and γ). Each vector represents either patient motion (e.g., in the case of externally measured motion) or patient motion relative to the gantry (e.g., if motion information is inferred from the images). The position error vector may represent patient-motion related error, dynamic gantry position errors, or both.

Returning to FIG. 9, as an initial step of the method 80, CB CT projection images are acquired (step 82). Next, a position error vector (i.e., a patient motion vector) is determined for each projection image (step 84). The position error vectors may be determined by a variety of means including external detectors and image analysis. In one embodiment, the method 80 uses the method 60 described above with respect to FIGS. 5-8 to complete this step.

Next, the method 80 combines the position error vector with parameters that describe static calibration parameters or information of the scanner geometry (e.g., constant over the course of the scan) to derive a projection matrix for each projection image (step 86). The parameters for the scanner geometry include the distance from the x-ray source to the center of rotation (DSO), the distance from the x-ray source to the detector (DSD), and the θ value for each projection image. The projection matrix describes how each x-ray travels from the x-source, through the patient, and lands on a specific spot on the detector panel. The projection matrix is equivalent to the matrix used to convert a virtual 3D volume into a 2D image on a computer screen in 3D computer graphics operations. An example projection matrix is set forth below:

$$\xi = A00*X + A01*Y + A02*Z + A03*1.0$$

$$\psi = A10*X + A11*Y + A12*Z + A13*1.0$$

$$\zeta = A20*X + A21*Y + A22*Z + A23*1.0$$

$$U = \xi/\zeta$$

$$V = \psi/\zeta$$

The coordinates X, Y, and Z represent the location of a point on the patient in 3D space, U and V represent the location of the same point on the 2D detector panel, and A00 through A23 represent components of the projection matrix for a given projection image.

After the projection matrix is created, the method 80 supplies the projection images and the corresponding projection matrices to a reconstruction process (88). The reconstruction process uses the projection images and the projection matrices to determine how to map each projection image voxel back onto the projection volume during a process called back-projection. Alternatively, the reconstruction process may use iterative reconstruction to correct and reconstruct the images, which uses the projection matrices to map pixel data to volume data. The reconstruction process outputs the reconstructed images, which are corrected based on the detected motion (data 90).

Even when patient motion is not measured, the method 80 provides a mechanism to correct for dynamic gantry errors as long as the gantry errors are repeatable scan-to-scan. The method 80 can also be further accelerated by using a graphic processing unit ("GPU") or other specialized parallel processing hardware. In addition, the image correction method 80 may be adapted to situations with incomplete motion data. For example, if the position of a marker is only known at the beginning and the end of the scan, intermediate projections images may be corrected by linearly interpolating the position error vectors associated with the projection image with known position error vectors of other projection images.

Although the patient motion vector derivation method 60 and the image correction method 80 have been disclosed for CB CT imaging, the methods are also useful for CT, MRI, ultrasound, other forms of medical imaging, and forms of non-medical imaging, such as photography. For example, the image correction method 80 may be used in imaging technology where a 3D volume is evaluated as a sequence of 2D images, including 3D ultrasounds and 3D optical coherence tomography.

Also, although FIG. 3 illustrates the ROM module 46 as storing separate modules (e.g., 50, 52, 54, and 56), it is possible to combine or separate the modules stored in the ROM module 46 or in other memory. For example, in some embodiments, the same module performs the patient motion vector derivation method 60 and the image correction method 80. In addition, the ROM module 46 can include other modules for performing functions other than those functions described above. Furthermore, in some embodiments, the modules are stored on a computer-readable disk and transferred to the RAM module 44 and/or the ROM module 46 for execution.

Thus, the invention provides, among other things, methods and systems for determining patient motion in an image and correcting and reconstructing the image based on the detected patient motion. Various features and advantages of the invention are set forth in the following claims.

APPENDIX A

```
% Load U and V data (n markers × m projections) into
load 'data\test.mat';

% Load Reference 3D X, Y, and Z positions of each marker (3 × n)
load data\RefLoc.mat;

% Scanner Geometry Parameters
DSD = 716.59;
DSO = 488.111;
SCANANGLE = 360.03;

% Global Parameters
numMarkers = size(u_mm,2);
numProj = size(u_mm,1);
theta = (−30:−(SCANANGLE/numProj):−30+(SCANANGLE/numProj)*numProj+1))'/180.0*pi;

% Initialize motion parameters to zero (first guess)
CU = zeros(size(u_mm,1),3);
CV = zeros(size(u_mm,1),3);

%The following starts the main iterative loop
for iter = 1:5
    %***** Solve for V associated parameters (Z, Alpha, and Beta)
    for j = 1:numProj
        for i = 1:numMarkers
            % The following are "pseudo-constants" in the linearized equations
            V1 = v_mm(j,i);
            XS = RefLoc(1,i)+CU(j,1);
            YS = RefLoc(2,i)+CU(j,2);
            Z0 = RefLoc(3,i);
            ZD = CV(j,1);
            a1 = CV(j,2);
            a2 = CV(j,3);
            h1 = 1−cos(CV(j,2));
            h2 = 1−cos(CV(j,3));
            g1 = CV(j,2) − sin(CV(j,2));
            g2 = CV(j,3) − sin(CV(j,3));
            s3 = sin(CU(j,3));
            c3 = cos(CU(j,3));
            s4 = sin(theta(j));
            c4 = cos(theta(j));

            Alpha_vect(j,i) = DSD*YS + V1*(−s4*c3*Z0 + c4*s3*Z0);
            Beta_vect(j,i) = DSD*XS + V1*(−s4*s3*Z0 − c4*c3*Z0);
            delZ_vect(j,i) = DSD;
            errorV_A(j,i) = (V1*DSO − DSD*Z0 + V1*(XS*(−s4*s3−c4*c3) + YS*(c4*s3−s4*c3)))...
                ...
                + (V1*(XS*(c4*c3*h2 + s4*s3*h2)...
                + YS*(c4*c3*g2*g1 − a2*c4*c3*g1 − s4*s3*g2*a1 − c4*c3*g2*a1 + s4*c3*h1...
                − a2*s4*s3*g1 + s4*s3*a2*a1 + c4*c3*a2*a1 + s4*s3*g2*g1 − c4*s3*h1)...
                + ZD*(c4*c3*a2 + s4*c3*a1 + s4*s3*g2*h1 − s4*c3*g1 + c4*c3*g2*h1 − c4*c3*g2...
                − s4*s3*g2 + c4*s3*g1 − s4*s3*a2*h1 − c4*s3*a1 + s4*s3*a2 − c4*c3*a2*h1)...
                + Z0*(−s4*s3*a2*h1 − c4*c3*a2*h1 − s4*c3*g1 − s4*s3*g2 ...
                + c4*c3*g2*h1 − c4*c3*g2 + c4*s3*g1 + s4*s3*g2*h1))...
                + DSD*(XS*g2+ YS*(h2*a1 − h2*g1 + g1) ...
                + ZD*(h1 − h2*h1 + h2)+ Z0*(h1 − h2*h1 + h2) ) );
        end

        BV = errorV_A(j,:)';
        AV = [delZ_vect(j,:); Alpha_vect(j,:); Beta_vect(j,:)]';
        CV(j,:) = (AV\BV)';
    end

    %***** Solve for U associated parameters (X, Y, and gamma)
    for j = 1:numProj
        for i = 1:numMarkers
            % The following are "pseudo-constants" in the linearized equations
```

APPENDIX A-continued

```
            U1 = u_mm(j,i);
            X0 = RefLoc(1,i);
            Y0 = RefLoc(2,i);
            XD = CU(j,2);
            YD = CU(j,2);
            ZS = RefLoc(3,i)+CV(j,1);
            c1 = cos(CV(j,2));
            s1 = sin(CV(j,2));
            c2 = cos(CV(j,3));
            s2 = sin(CV(j,3));
            a3 = CU(j,3);
            g3 = a3 − sin(a3);
            h3 = 1−cos(a3);
            s4 = sin(theta(j));
            c4 = cos(theta(j));

            delX_vect(j,i) = (U1*c2*c4 − DSD*c2*s4);
            delY_vect(j,i) = (U1*c1*s4 − U1*s1*s2*c4 + DSD*s1*s2*s4 + DSD*c1*c4);
            gamma_vect(j,i) = (U1*(X0*c2*s4 − Y0*s1*s2*s4 − Y0*c1*c4+ ZS*s1*c4 − ZS*c1*s2*s4)...
                +DSD*(X0*c2*c4 + Y0*c1*s4 − Y0*s1*s2*c4 − ZS*s1*s4 − ZS*c1*s2*c4));
            errorU_vect(j,i) = U1*DSO − U1*(X0*c2*c4 − Y0*s1*s2*c4 + Y0*c1*s4 − ZS*s1*s4...
                − ZS*c1*s2*c4)...
                − DSD*(−X0*c2*s4 + Y0*c1*c4 + Y0*s1*s2*s4 + ZS*c1*s2*s4 − ZS*s1*c4)...
                ...
                + U1*(XD*(−c2*s4*a3 + c2*s4*g3 + c2*c4*h3) ...
                + X0*(c2*c4*h3 + c2*s4*g3)...
                + YD*(c1*c4*a3 − s2*s1*c4*h3 + s2*s1*s4*a3 + s2*s1*s4*g3 − c1*c4*g3...
                + c1*s4*h3)...
                + Y0*(−s2*s1*s4*g3 − s2*s1*c4*h3 − c1*c4*g3 + c1*s4*h3 ) ...
                + ZS*(−s1*s4*h3 − s2*c1*c4*h3 + s1*c4*g3 − s2*c1*s4*g3 ) )...
                ...
                + DSD*(XD*(c2*c4*g3 − c2*c4*a3 − c2*s4*h3) + X0*(c2*c4*g3 − c2*s4*h3)...
                + YD*(−c1*s4*a3 + c1*c4*h3 + c1*s4*g3 + s2*s1*c4*a3 + s2*s1*s4*h3...
                − s2*s1*c4*g3)...
                + Y0*(c1*c4*h3 + s2*s1*s4*h3 − s2*s1*c4*g3 + c1*s4*g3)...
                + ZS*(−s1*s4*g3 − s2*c1*c4*g3 + s2*c1*s4*h3 − s1*c4*h3) )...
                ;
        end

        AU = [delX_vect(j,:); delY_vect(j,:); gamma_vect(j,:)]';
        BU = errorU_vect(j,:)';
        CU(j,:) = (AU\BU)';
    end
end

figure; plot([CV(:,2), CV(:,3), CU(:,3)] * 180/pi);
title('Motion Angles: Alpha, Beta, and Gamma');

figure; plot([CU(:,1), CU(:,2), CV(:,1)]);
title('Motion Translations: X, Y, and Z');
```

What is claimed is:

1. A method for determining patient motion in an image, the method executed by an imaging system including a scanner having a detector panel and configured to conduct a scan of a patient, a computer with an electronic processing unit, and a memory module storing a motion vector extraction module executable by the electronic processing unit, the method comprising:

obtaining, at the computer, an image based on image data generated by the scanner during a patient scan, the image including at least three markers assumed to be in a rigid or semi-rigid configuration, each of the at least three markers having actual measured positions on the detector panel of the scanner in a first dimension and a second dimension;

determining, with the electronic processing unit, a reference three-dimensional position for each of the at least three markers;

defining, with the electronic processing unit, linearized equations describing the relationship between the reference three-dimensional position and the actual measured positions of each of the at least three markers, geometric parameters of the scanner, and patient motion; and solving, with the electronic processing unit, the linearized equations to derive a motion vector describing patient motion that occurred during the patient scan for the image that accounts for differences between the reference three-dimensional position of each of the at least three markers and the actual measured positions for each of the at least three markers, wherein solving the linearized equations to derive a motion vector includes iteratively updating and solving the linearized equations until reaching a convergence.

2. The method of claim 1, wherein each of the at least three markers has a reference three-dimensional position $X_i$, $Y_i$, $Z_i$, and measured positions on a detector panel of the scanner in a first dimension $U_m$ and a second dimension $V_m$, wherein the motion vector includes ΔX, ΔY, ΔZ, α, β, and γ, wherein α, β, and γ represent rotational motion of the patient, and wherein iteratively updating and solving the linearized equations includes:

(a) assuming a value of $\Delta X$, a value of $\Delta Y$, and a value of $\gamma$, (b) calculating a value for $\Delta Z$, a value for $\alpha$, and a value for $\beta$ using the assumed values of $\Delta X$, $\Delta Y$, and $\gamma$ and one of the linearized equations defining positions in the second dimension, and (c) calculating a value for $\Delta X$, a value for $\Delta Y$, and a value for $\gamma$ using the calculated values of $\Delta Z$, $\alpha$, and $\beta$ and one of the linearized equations defining positions in the first dimension.

3. The method of claim 2, wherein iteratively updating and solving the linearized equations further includes repeating steps (b) through (c) at least once.

4. The method of claim 2, wherein solving the linearized equations to derive a motion vector includes approximating sines and cosines in rotational transformations using a Taylor expansion consisting of a linear first term and an estimated residual.

5. The method of claim 4, wherein solving the linearized equations to derive a motion vector further includes updating the residuals of the approximated sines and cosines during each repetition of steps (b) through (c).

6. The method of claim 4, wherein approximating the sines and cosines in the rotational transformations using the Taylor expansion includes using an estimated residual that is constant.

7. The method of claim 1, wherein the image obtained at the computer includes a projection image.

8. A system for determining patient motion in an image, the system comprising:

a scanner having a detector panel; and a computer including an electronic processing unit, a memory module, and an input/output interface, where the memory module is configured to store a motion vector extraction module that is executed by the electronic processing unit;

wherein the scanner is configured to obtain and send to the computer an image based on image data generated by the scanner during a scan of a patient, the image including at least three markers assumed to be in a rigid or semi-rigid configuration, each of the at least three markers having actual measured positions on the detector panel of the scanner in a first dimension and a second dimension, wherein the electronic processing unit is configured to determine a reference three-dimensional position for each of the at least three markers, wherein the electronic processing unit is configured to define linearized equations describing the relationship between the reference three-dimensional position and the actual measured positions of each of the at least three markers, geometric parameters of the scanner, and patient motion, wherein, the electronic processing unit is configured to solve the linearized equations to derive a motion vector describing patient motion that occurred during the patient scan for the image that accounts for differences between the reference three-dimensional position of each of the at least three markers and the actual measured positions for each of the at least three markers, and wherein solving the linearized equations to derive a motion vector includes iteratively updating and solving the linearized equations until reaching a convergence.

9. The system according to claim 8, wherein each of the at least three markers has a reference three-dimensional position $X_i$, $Y_i$, $Z_i$ and measured positions on a detector panel of the scanner in a first dimension $U_m$ and a second dimension $V_m$, wherein the motion vector includes $\Delta X$, $\Delta Y$, $\Delta Z$, $\alpha$, $\beta$, and $\gamma$, wherein $\alpha$, $\beta$, and $\gamma$ represent rotational motion of the patient, and-the electronic processing unit is configured to iteratively update and solve linearized equations by:

(a) assuming a value of $\Delta X$, a value of $\Delta Y$, and a value of $\gamma$, (b) calculating a value for $\Delta Z$, a value of $\alpha$, and a value of $\beta$ using the assumed values of $\Delta X$, $\Delta Y$, and $\gamma$ and one of the linearized equations defining positions in the second dimension, and (c) calculating a value for $\Delta X$, a value of $\Delta Y$, and a value of $\gamma$ using the calculated values of $\Delta Z$, $\alpha$, and $\beta$ and one of the linearized equations defining positions in the first dimension.

10. The system according to claim 9, wherein the electronic processing unit is further configured to iteratively update and solve linearized equations by repeating steps (b) through (c) at least once.

11. The system according to claim 9, wherein the electronic processing unit is configured to solve numerically the linearized equations to derive a motion vector by approximating sines and cosines in rotational transformations using a Taylor expansion consisting of a linear first term and an estimated residual.

12. The system according to claim 11, wherein the electronic processing unit is further configured to solve numerically the linearized equations to derive a motion vector by updating the residuals of the approximated sines and cosines during each repetition of steps (b) through (c).

13. The system according to claim 11, wherein the electronic processing unit is configured to approximate the sines and cosines in the rotational transformations using a Taylor expansion by using an estimated residual that is constant.

14. The method of claim 1, further comprising: positioning at least three fiducial markers on the patient before the step of obtaining the image based on image data, wherein the at least three fiducial markers appear as the at least three markers on the image.

15. The system of claim 8, further comprising: wherein the patient has at least three fiducial markers positioned thereon and the at least three fiducial markers appear as the at least three markers on the image.

16. The method of claim 1, wherein each of the at least three markers has a reference three-dimensional position $X_i$, $Y_i$, $Z_i$, and measured positions on a detector panel of the scanner in a first dimension $U_m$ and a second dimension $V_m$, the motion vector includes $\Delta X$, $\Delta Y$, $\Delta Z$, $\alpha$, $\beta$, and $\gamma$, wherein $\alpha$, $\beta$, and $\gamma$ represent rotational motion of the patient, and iteratively updating and solving linearized equations until reaching a convergence includes iteratively solving a linearized $V_m$ equation to calculate a value for $\Delta Z$, a value of $\alpha$, and a value of $\beta$ and solving a linearized $U_m$ equation to calculate a value of $\Delta X$, a value of $\Delta Y$, and a value of $\gamma$.

17. The method of claim 16, wherein, after an initial solving of one of the linearized $V_m$ equation and linearized $U_m$ equation based on assumed values, solving the linearized $V_m$ equation is based on a previously calculated $\Delta X$ value, $\Delta Y$ value, and $\gamma$ value determined by solving the linearized $U_m$ equation, and solving the linearized $U_m$ equation is based on a previously calculated $\Delta Z$, value of $\alpha$, and value of $\beta$ determined by solving the linearized $V_m$ equation.

18. The system of claim 8, wherein each of the at least three markers has a reference three-dimensional position $X_i$, $Y_i$, $Z_i$ and measured positions on a detector panel of the scanner in a first dimension $U_m$ and a second dimension $V_m$, the motion vector includes ΔX, ΔY, ΔZ, α, β, and γ, wherein α, β, and γ represent rotational motion of the patient, and iteratively updating and solving linearized equations until reaching a convergence includes iteratively solving a linearized $V_m$ equation to calculate a value for ΔZ, a value of α, and a value of β and solving a linearized $U_m$ equation to calculate a value of ΔX, a value of ΔY, and a value of γ.

19. The system of claim 18, wherein, after an initial solving of one of the linearized $V_m$ equation and linearized $U_m$ equation based on assumed values, solving the linearized $V_m$ equation is based on a previously calculated ΔX value, ΔY value, and γ value determined by solving the linearized $U_m$ equation, and solving the linearized $U_m$ equation is based on a previously calculated ΔZ, value of α, and value of β determined by solving the linearized $V_m$ equation.

20. The method of claim 1, further comprising: displaying a motion-corrected image generated based on the derived motion vector.

21. The system of claim 8, further comprising: a display that displays a motion-corrected image generated based on the derived motion vector.

* * * * *